United States Patent
Villavicencio

(10) Patent No.: US 11,812,923 B2
(45) Date of Patent: Nov. 14, 2023

(54) SPINAL FIXATION DEVICE

(71) Applicant: Alan Villavicencio, Boulder, CO (US)

(72) Inventor: Alan Villavicencio, Boulder, CO (US)

( * ) Notice: Subject to any disclaimer, the term of this patent is extended or adjusted under 35 U.S.C. 154(b) by 397 days.

(21) Appl. No.: 13/648,068

(22) Filed: Oct. 9, 2012

(65) Prior Publication Data

US 2013/0090689 A1    Apr. 11, 2013

Related U.S. Application Data

(60) Provisional application No. 61/558,736, filed on Nov. 11, 2011, provisional application No. 61/544,920, filed on Oct. 7, 2011.

(51) Int. Cl.
*A61B 17/70* (2006.01)
*A61B 17/86* (2006.01)

(52) U.S. Cl.
CPC ...... *A61B 17/7068* (2013.01); *A61B 17/8685* (2013.01)

(58) Field of Classification Search
CPC ............ A61B 17/7064; A61B 17/7068; A61B 17/7067; A61B 17/70; A61B 17/7062
USPC .................................................. 606/247–249
See application file for complete search history.

(56) References Cited

U.S. PATENT DOCUMENTS

| | | |
|---|---|---|
| 765,879 A | 7/1904 | Campbell |
| 832,201 A | 10/1906 | Kistler |
| 1,137,585 A | 4/1915 | Thornton, Jr. |
| 1,331,737 A | 2/1920 | Emil |
| 1,400,648 A | 12/1921 | Whitney |
| 1,725,670 A | 8/1929 | William |
| 1,737,488 A | 11/1929 | Zohlen |
| 2,137,121 A | 11/1938 | Greenwald |
| 2,677,369 A | 5/1954 | Knowles |
| 2,689,568 A | 9/1954 | Wakefield |
| 2,774,350 A | 12/1956 | Cleveland, Jr. |
| 2,789,860 A | 4/1957 | Knowles |
| 3,025,853 A | 3/1962 | Mason |
| 3,039,468 A | 6/1962 | Price |
| 3,242,922 A | 3/1966 | Thomas |
| 3,409,013 A | 11/1968 | Berry |
| 3,628,535 A | 12/1971 | Ostrowsky et al. |

(Continued)

FOREIGN PATENT DOCUMENTS

| | | |
|---|---|---|
| CN | 101129271 | 2/2008 |
| EP | 1266606 A2 | 12/2002 |

(Continued)

OTHER PUBLICATIONS

"Australian Application Serial No. 2007343630, First Examiner Report dated Jun. 28, 2012", 5 pgs.

(Continued)

*Primary Examiner* — Eduardo C Robert
*Assistant Examiner* — Michelle C Eckman
(74) *Attorney, Agent, or Firm* — Perkins Coie LLP

(57) ABSTRACT

A spinal fixation device includes a pair of substantially s-shaped plates, each plate having an outer surface and a bone contact surface and at least one aperture therethrough. A bolt joins the plates at a desired orientation, through the aperture. The bolt includes a head with a rounded or beveled base for facilitating fixation of the plates with a spinous processes while the plates are tilted or rotated with respect to one another and the spinal column.

13 Claims, 13 Drawing Sheets

(56) References Cited

U.S. PATENT DOCUMENTS

| | | | |
|---|---|---|---|
| 3,648,691 A * | 3/1972 | Lumb et al. | 606/279 |
| 3,788,318 A | 1/1974 | Kim | |
| 3,789,852 A | 2/1974 | Kim | |
| 4,092,788 A | 6/1978 | Gowing | |
| 4,269,178 A | 5/1981 | Keene | |
| 4,274,401 A | 6/1981 | Miskew | |
| 4,369,769 A | 1/1983 | Edwards | |
| 4,369,770 A | 1/1983 | Bacal et al. | |
| 4,409,968 A | 10/1983 | Drummond | |
| 4,448,191 A | 5/1984 | Rodnyansky et al. | |
| 4,554,914 A * | 11/1985 | Kapp et al. | 606/86 A |
| 4,570,618 A | 2/1986 | Wu | |
| 4,573,454 A | 3/1986 | Hoffman | |
| 4,599,086 A | 7/1986 | Doty | |
| 4,636,217 A | 1/1987 | Ogilvie et al. | |
| 4,697,582 A | 10/1987 | William | |
| 4,773,402 A | 9/1988 | Asher et al. | |
| 4,892,545 A | 1/1990 | Day et al. | |
| 5,007,909 A | 4/1991 | Rogozinski | |
| 5,010,879 A | 4/1991 | Moriya et al. | |
| 5,011,484 A | 4/1991 | Breard | |
| 5,030,220 A | 7/1991 | Howland | |
| 5,062,850 A | 11/1991 | MacMillan et al. | |
| 5,306,275 A | 4/1994 | Bryan | |
| 5,390,683 A | 2/1995 | Pisharodi | |
| 5,413,576 A | 5/1995 | Rivard | |
| 5,472,426 A | 12/1995 | Bonati et al. | |
| 5,496,318 A | 3/1996 | Howland et al. | |
| 5,503,617 A | 4/1996 | Jako | |
| 5,527,312 A | 6/1996 | Ray | |
| 5,540,703 A | 7/1996 | Barker, Jr. et al. | |
| 5,609,634 A | 3/1997 | Voydeville | |
| 5,609,636 A | 3/1997 | Kohrs et al. | |
| 5,628,756 A | 5/1997 | Barker, Jr. et al. | |
| 5,645,599 A | 7/1997 | Samani | |
| 5,653,763 A | 8/1997 | Errico et al. | |
| 5,658,335 A | 8/1997 | Allen | |
| 5,702,452 A | 12/1997 | Argenson et al. | |
| 5,702,453 A | 12/1997 | Rabbe et al. | |
| 5,716,358 A | 2/1998 | Ochoa et al. | |
| 5,725,582 A | 3/1998 | Bevan et al. | |
| 5,800,550 A | 9/1998 | Sertich | |
| 5,813,978 A | 9/1998 | Jako | |
| 5,836,948 A | 11/1998 | Zucherman et al. | |
| 5,860,977 A | 1/1999 | Zucherman et al. | |
| 5,876,404 A | 3/1999 | Zucherman et al. | |
| 5,928,232 A | 7/1999 | Howland et al. | |
| 5,976,146 A | 11/1999 | Ogawa et al. | |
| 5,989,256 A | 11/1999 | Kuslich et al. | |
| 6,045,442 A | 4/2000 | Bounds | |
| 6,045,552 A | 4/2000 | Zucherman et al. | |
| 6,048,342 A | 4/2000 | Zucherman et al. | |
| 6,067,390 A | 5/2000 | Hames et al. | |
| 6,068,630 A | 5/2000 | Zucherman et al. | |
| 6,074,390 A | 6/2000 | Zucherman et al. | |
| 6,090,112 A | 7/2000 | Zucherman et al. | |
| 6,099,527 A | 8/2000 | Hochschuler et al. | |
| 6,102,950 A | 8/2000 | Vaccaro | |
| 6,132,464 A | 10/2000 | Fairant | |
| 6,149,652 A | 11/2000 | Zucherman et al. | |
| 6,152,926 A | 11/2000 | Zucherman et al. | |
| 6,156,038 A | 12/2000 | Zucherman et al. | |
| 6,176,882 B1 | 1/2001 | Biedermann et al. | |
| 6,183,471 B1 | 2/2001 | Zucherman et al. | |
| 6,190,387 B1 | 2/2001 | Zucherman et al. | |
| 6,200,322 B1 | 3/2001 | Branch et al. | |
| 6,231,610 B1 | 5/2001 | Geisler | |
| 6,235,030 B1 | 5/2001 | Zucherman et al. | |
| 6,235,059 B1 | 5/2001 | Benezech et al. | |
| 6,238,397 B1 | 5/2001 | Zucherman et al. | |
| 6,277,094 B1 | 8/2001 | Schendel | |
| 6,280,444 B1 | 8/2001 | Zucherman et al. | |
| 6,312,431 B1 * | 11/2001 | Asfora | 606/279 |
| 6,332,882 B1 | 12/2001 | Zucherman et al. | |
| 6,332,883 B1 | 12/2001 | Zucherman et al. | |
| 6,340,362 B1 | 1/2002 | Pierer et al. | |
| 6,364,883 B1 | 4/2002 | Santilli | |
| 6,375,682 B1 | 4/2002 | Fleischmann et al. | |
| 6,379,355 B1 | 4/2002 | Zucherman et al. | |
| 6,398,811 B1 | 6/2002 | McKay | |
| 6,416,776 B1 | 7/2002 | Shamie | |
| 6,419,676 B1 | 7/2002 | Zucherman et al. | |
| 6,419,677 B2 | 7/2002 | Zucherman et al. | |
| 6,440,169 B1 | 8/2002 | Elberg et al. | |
| 6,451,019 B1 | 9/2002 | Zucherman et al. | |
| 6,451,020 B1 | 9/2002 | Zucherman et al. | |
| 6,451,021 B1 | 9/2002 | Ralph et al. | |
| 6,478,796 B2 | 11/2002 | Zucherman et al. | |
| 6,500,178 B2 | 12/2002 | Zucherman et al. | |
| 6,514,255 B1 | 2/2003 | Ferree | |
| 6,514,256 B2 | 2/2003 | Zucherman et al. | |
| 6,520,907 B1 | 2/2003 | Foley et al. | |
| 6,582,433 B2 | 6/2003 | Yun | |
| 6,589,243 B1 | 7/2003 | Viart et al. | |
| 6,599,294 B2 | 7/2003 | Fuss et al. | |
| 6,626,944 B1 | 9/2003 | Taylor | |
| 6,652,527 B2 | 11/2003 | Zucherman et al. | |
| 6,652,534 B2 | 11/2003 | Zucherman et al. | |
| 6,656,185 B2 | 12/2003 | Gleason et al. | |
| 6,669,729 B2 | 12/2003 | Chin | |
| 6,679,833 B2 | 1/2004 | Smith et al. | |
| 6,682,563 B2 | 1/2004 | Scharf | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,712,819 B2 | 3/2004 | Zucherman et al. | |
| 6,733,534 B2 | 5/2004 | Sherman | |
| 6,746,485 B1 | 6/2004 | Zucherman et al. | |
| 6,761,720 B1 | 7/2004 | Senegas | |
| 6,796,983 B1 | 9/2004 | Zucherman et al. | |
| 6,800,084 B2 | 10/2004 | Davison et al. | |
| 6,835,205 B2 | 12/2004 | Atkinson et al. | |
| 6,902,566 B2 | 6/2005 | Zucherman et al. | |
| 6,902,580 B2 | 6/2005 | Fallin et al. | |
| 6,926,728 B2 | 8/2005 | Zucherman et al. | |
| 6,946,000 B2 | 9/2005 | Senegas et al. | |
| 6,966,929 B2 | 11/2005 | Mitchell | |
| 6,989,011 B2 | 1/2006 | Paul et al. | |
| 7,008,431 B2 | 3/2006 | Simonson | |
| 7,029,473 B2 | 4/2006 | Zucherman et al. | |
| 7,048,736 B2 | 5/2006 | Robinson et al. | |
| 7,083,649 B2 | 8/2006 | Zucherman et al. | |
| 7,087,083 B2 | 8/2006 | Pasquet et al. | |
| 7,101,375 B2 | 9/2006 | Zucherman et al. | |
| 7,131,972 B2 | 11/2006 | Mazda et al. | |
| 7,163,558 B2 | 1/2007 | Senegas et al. | |
| 7,189,234 B2 | 3/2007 | Zucherman et al. | |
| 7,201,751 B2 | 4/2007 | Zucherman et al. | |
| 7,238,204 B2 | 7/2007 | Le Couedic et al. | |
| 7,306,628 B2 | 12/2007 | Zucherman et al. | |
| 7,335,203 B2 | 2/2008 | Winslow et al. | |
| 7,442,208 B2 | 10/2008 | Mathieu et al. | |
| 7,458,981 B2 | 12/2008 | Fielding et al. | |
| 7,473,268 B2 | 1/2009 | Zucherman et al. | |
| 7,476,251 B2 | 1/2009 | Zucherman et al. | |
| 7,481,839 B2 | 1/2009 | Zucherman et al. | |
| 7,510,567 B2 | 3/2009 | Zucherman et al. | |
| 7,520,887 B2 | 4/2009 | Maxy et al. | |
| 7,530,991 B2 | 5/2009 | Nekozuka et al. | |
| 7,537,613 B2 | 5/2009 | Arnin et al. | |
| 7,549,999 B2 | 6/2009 | Zucherman et al. | |
| 7,585,313 B2 | 9/2009 | Kwak et al. | |
| 7,585,316 B2 | 9/2009 | Trieu | |
| 7,588,592 B2 | 9/2009 | Winslow et al. | |
| 7,621,939 B2 | 11/2009 | Zucherman et al. | |
| 7,628,816 B2 * | 12/2009 | Magerl et al. | 623/17.16 |
| 7,635,377 B2 | 12/2009 | Zucherman et al. | |
| 7,635,378 B2 | 12/2009 | Zucherman et al. | |
| 7,637,912 B2 | 12/2009 | Iwasaki et al. | |
| 7,658,752 B2 | 2/2010 | Labrom et al. | |
| 7,753,938 B2 | 7/2010 | Aschmann et al. | |
| 7,799,058 B2 | 9/2010 | Froehlich et al. | |
| 7,871,426 B2 | 1/2011 | Chin et al. | |
| 7,918,875 B2 | 4/2011 | Lins et al. | |

(56) References Cited

U.S. PATENT DOCUMENTS

| | | |
|---|---|---|
| 7,922,745 B2 | 4/2011 | Hestad et al. |
| 7,922,750 B2 | 4/2011 | Trautwein et al. |
| 7,927,354 B2 | 4/2011 | Edidin et al. |
| 7,931,674 B2 | 4/2011 | Zucherman et al. |
| 7,955,392 B2 | 6/2011 | Dewey et al. |
| 7,959,652 B2 | 6/2011 | Zucherman et al. |
| 8,007,517 B2 | 8/2011 | Lins et al. |
| 8,012,207 B2 | 9/2011 | Kim |
| 8,048,120 B1 | 11/2011 | Fallin et al. |
| 8,075,593 B2 | 12/2011 | Hess |
| 8,105,382 B2 | 1/2012 | Olmos et al. |
| 8,167,915 B2 | 5/2012 | Ferree et al. |
| 8,241,330 B2 | 8/2012 | Lamborne et al. |
| 8,343,190 B1 * | 1/2013 | Mueller et al. ............... 606/248 |
| 8,382,801 B2 | 2/2013 | Lamborne et al. |
| 8,403,959 B2 | 3/2013 | Dollinger |
| 9,055,981 B2 | 6/2015 | Lamborne et al. |
| 9,247,968 B2 | 2/2016 | Taber et al. |
| 9,265,532 B2 | 2/2016 | Lamborne et al. |
| 9,724,136 B2 | 8/2017 | Taber et al. |
| 9,743,960 B2 | 8/2017 | Lamborne et al. |
| 9,770,271 B2 | 9/2017 | Lamborne et al. |
| 9,861,400 B2 | 1/2018 | Lamborne et al. |
| 2001/0007070 A1 | 7/2001 | Stewart et al. |
| 2001/0007073 A1 | 7/2001 | Zucherman et al. |
| 2001/0012938 A1 | 8/2001 | Zucherman et al. |
| 2001/0016743 A1 | 8/2001 | Zucherman et al. |
| 2001/0016776 A1 | 8/2001 | Zuckerman et al. |
| 2001/0020170 A1 | 9/2001 | Zucherman et al. |
| 2001/0021850 A1 | 9/2001 | Zucherman et al. |
| 2001/0021851 A1 | 9/2001 | Eberlein et al. |
| 2001/0031965 A1 | 10/2001 | Zucherman et al. |
| 2001/0039452 A1 | 11/2001 | Zucherman et al. |
| 2002/0029039 A1 | 3/2002 | Zucherman et al. |
| 2002/0029081 A1 | 3/2002 | Scarborough et al. |
| 2002/0045899 A1 | 4/2002 | Errico et al. |
| 2002/0095154 A1 | 7/2002 | Atkinson et al. |
| 2002/0111679 A1 | 8/2002 | Zucherman et al. |
| 2002/0116000 A1 | 8/2002 | Zucherman et al. |
| 2002/0143331 A1 | 10/2002 | Zucherman et al. |
| 2002/0183218 A1 | 12/2002 | Farrell et al. |
| 2002/0183746 A1 | 12/2002 | Zucherman et al. |
| 2003/0040746 A1 | 2/2003 | Mitchell et al. |
| 2003/0045935 A1 | 3/2003 | Angelucci et al. |
| 2003/0065330 A1 | 4/2003 | Zucherman et al. |
| 2003/0065396 A1 | 4/2003 | Michelson |
| 2003/0083688 A1 | 5/2003 | Simonson |
| 2003/0139812 A1 | 7/2003 | Garcia et al. |
| 2003/0153912 A1 | 8/2003 | Graf |
| 2003/0153915 A1 | 8/2003 | Nekozuka et al. |
| 2003/0216736 A1 | 11/2003 | Robinson et al. |
| 2003/0220643 A1 | 11/2003 | Ferree |
| 2004/0024458 A1 | 2/2004 | Senegas et al. |
| 2004/0059339 A1 | 3/2004 | Roehm, III et al. |
| 2004/0093001 A1 | 5/2004 | Hamada |
| 2004/0097931 A1 | 5/2004 | Mitchell |
| 2004/0106995 A1 | 6/2004 | Le Couedic et al. |
| 2004/0119121 A1 | 6/2004 | Kariyazono |
| 2004/0138749 A1 | 7/2004 | Zucherman et al. |
| 2004/0138750 A1 | 7/2004 | Mitchell |
| 2004/0143270 A1 | 7/2004 | Zucherman et al. |
| 2004/0147937 A1 | 7/2004 | Dunbar et al. |
| 2004/0153071 A1 | 8/2004 | Zucherman et al. |
| 2004/0162617 A1 | 8/2004 | Zucherman et al. |
| 2004/0167520 A1 | 8/2004 | Zucherman et al. |
| 2004/0167521 A1 | 8/2004 | De Windt |
| 2004/0172135 A1 | 9/2004 | Mitchell |
| 2004/0181282 A1 | 9/2004 | Zucherman et al. |
| 2004/0193159 A1 | 9/2004 | Zucherman et al. |
| 2004/0199121 A1 | 10/2004 | Wenchell et al. |
| 2004/0199168 A1 | 10/2004 | Bertagnoli et al. |
| 2004/0220568 A1 | 11/2004 | Zucherman et al. |
| 2004/0220577 A1 | 11/2004 | Cragg et al. |
| 2004/0249379 A1 | 12/2004 | Winslow et al. |
| 2005/0010293 A1 | 1/2005 | Zucherman et al. |
| 2005/0010296 A1 | 1/2005 | Mitchell |
| 2005/0010298 A1 | 1/2005 | Zucherman et al. |
| 2005/0075634 A1 | 4/2005 | Zucherman et al. |
| 2005/0085855 A1 | 4/2005 | Forsberg |
| 2005/0101955 A1 | 5/2005 | Zucherman et al. |
| 2005/0113926 A1 | 5/2005 | Zucherman et al. |
| 2005/0125065 A1 | 6/2005 | Zucherman et al. |
| 2005/0131421 A1 | 6/2005 | Anderson et al. |
| 2005/0143738 A1 | 6/2005 | Zucherman et al. |
| 2005/0143740 A1 | 6/2005 | Morris et al. |
| 2005/0143820 A1 | 6/2005 | Zucherman et al. |
| 2005/0143826 A1 | 6/2005 | Zucherman et al. |
| 2005/0143827 A1 | 6/2005 | Globerman et al. |
| 2005/0149192 A1 | 7/2005 | Zucherman et al. |
| 2005/0149193 A1 | 7/2005 | Zucherman et al. |
| 2005/0149196 A1 | 7/2005 | Zucherman et al. |
| 2005/0154462 A1 | 7/2005 | Zucherman et al. |
| 2005/0165398 A1 | 7/2005 | Reiley |
| 2005/0192574 A1 | 9/2005 | Blain |
| 2005/0192586 A1 | 9/2005 | Zucherman et al. |
| 2005/0196420 A1 | 9/2005 | Zucherman et al. |
| 2005/0203512 A1 | 9/2005 | Hawkins et al. |
| 2005/0203624 A1 | 9/2005 | Serhan et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0234452 A1 | 10/2005 | Malandain |
| 2005/0240182 A1 | 10/2005 | Zucherman et al. |
| 2005/0245929 A1 | 11/2005 | Winslow et al. |
| 2005/0245937 A1 | 11/2005 | Winslow |
| 2005/0261768 A1 | 11/2005 | Trieu |
| 2005/0283237 A1 | 12/2005 | Zucherman et al. |
| 2005/0283242 A1 | 12/2005 | Zucherman et al. |
| 2005/0283243 A1 | 12/2005 | Zucherman et al. |
| 2005/0288672 A1 | 12/2005 | Ferree |
| 2006/0004447 A1 | 1/2006 | Mastrorio et al. |
| 2006/0015099 A1 | 1/2006 | Cannon et al. |
| 2006/0015181 A1 | 1/2006 | Elberg |
| 2006/0036246 A1 | 2/2006 | Carl et al. |
| 2006/0036258 A1 | 2/2006 | Zucherman et al. |
| 2006/0036259 A1 | 2/2006 | Carl et al. |
| 2006/0036324 A1 | 2/2006 | Sachs et al. |
| 2006/0058790 A1 | 3/2006 | Carl et al. |
| 2006/0064165 A1 | 3/2006 | Zucherman et al. |
| 2006/0064166 A1 | 3/2006 | Zucherman et al. |
| 2006/0084983 A1 | 4/2006 | Kim |
| 2006/0084985 A1 | 4/2006 | Kim |
| 2006/0084988 A1 | 4/2006 | Kim |
| 2006/0084994 A1 | 4/2006 | Atkinson et al. |
| 2006/0085069 A1 | 4/2006 | Kim |
| 2006/0085070 A1 | 4/2006 | Kim |
| 2006/0089654 A1 | 4/2006 | Lins et al. |
| 2006/0089718 A1 | 4/2006 | Zucherman et al. |
| 2006/0106361 A1 | 5/2006 | Muni et al. |
| 2006/0106381 A1 | 5/2006 | Ferree et al. |
| 2006/0106397 A1 | 5/2006 | Lins |
| 2006/0122606 A1 | 6/2006 | Wolgen |
| 2006/0122620 A1 | 6/2006 | Kim |
| 2006/0124247 A1 | 6/2006 | Collins et al. |
| 2006/0136060 A1 | 6/2006 | Taylor |
| 2006/0142761 A1 | 6/2006 | Landry et al. |
| 2006/0161154 A1 | 7/2006 | McAfee |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0235387 A1 | 10/2006 | Peterman |
| 2006/0235400 A1 | 10/2006 | Schneider |
| 2006/0235409 A1 | 10/2006 | Blain |
| 2006/0235521 A1 | 10/2006 | Zucherman et al. |
| 2006/0235533 A1 | 10/2006 | Blain |
| 2006/0241601 A1 | 10/2006 | Trautwein et al. |
| 2006/0241610 A1 | 10/2006 | Lim et al. |
| 2006/0241757 A1 | 10/2006 | Anderson |
| 2006/0247623 A1 | 11/2006 | Anderson et al. |
| 2006/0247634 A1 | 11/2006 | Warner et al. |
| 2006/0247640 A1 | 11/2006 | Blackwell et al. |

(56) References Cited

U.S. PATENT DOCUMENTS

| | | |
|---|---|---|
| 2006/0259037 A1 | 11/2006 | Hartmann et al. |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271049 A1 | 11/2006 | Zucherman et al. |
| 2006/0271055 A1 | 11/2006 | Thramann |
| 2006/0271194 A1 | 11/2006 | Zucherman et al. |
| 2006/0282079 A1 | 12/2006 | Labrom et al. |
| 2006/0293662 A1 | 12/2006 | Boyer, II et al. |
| 2007/0005064 A1 | 1/2007 | Anderson et al. |
| 2007/0010813 A1 | 1/2007 | Zucherman et al. |
| 2007/0016303 A1 | 1/2007 | Jackson |
| 2007/0032790 A1 | 2/2007 | Aschmann et al. |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0049934 A1 | 3/2007 | Edidin et al. |
| 2007/0049935 A1 | 3/2007 | Edidin et al. |
| 2007/0049943 A1 | 3/2007 | Moskowitz et al. |
| 2007/0055237 A1 | 3/2007 | Edidin et al. |
| 2007/0055246 A1 | 3/2007 | Zucherman et al. |
| 2007/0055276 A1 | 3/2007 | Edidin |
| 2007/0073292 A1 | 3/2007 | Kohm et al. |
| 2007/0093823 A1 | 4/2007 | Booth et al. |
| 2007/0093825 A1 | 4/2007 | Ferree et al. |
| 2007/0093828 A1 | 4/2007 | Abdou |
| 2007/0093830 A1 | 4/2007 | Zucherman et al. |
| 2007/0100340 A1 | 5/2007 | Lange et al. |
| 2007/0106298 A1 | 5/2007 | Carli et al. |
| 2007/0106385 A1 | 5/2007 | Zucherman et al. |
| 2007/0118120 A1 | 5/2007 | Stevenson et al. |
| 2007/0123861 A1 | 5/2007 | Dewey et al. |
| 2007/0142915 A1 | 6/2007 | Altarac et al. |
| 2007/0149972 A1 | 6/2007 | Nakajima et al. |
| 2007/0152001 A1 | 7/2007 | Cho et al. |
| 2007/0161993 A1 | 7/2007 | Ravikumar |
| 2007/0162000 A1 | 7/2007 | Perkins |
| 2007/0162001 A1 * | 7/2007 | Chin et al. .................. 606/61 |
| 2007/0162005 A1 | 7/2007 | Peterson et al. |
| 2007/0167945 A1 | 7/2007 | Lange et al. |
| 2007/0173818 A1 | 7/2007 | Hestad et al. |
| 2007/0173821 A1 | 7/2007 | Trieu |
| 2007/0173823 A1 | 7/2007 | Dewey et al. |
| 2007/0173832 A1 | 7/2007 | Tebbe et al. |
| 2007/0179500 A1 | 8/2007 | Chin et al. |
| 2007/0185490 A1 | 8/2007 | Implicito |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0191847 A1 | 8/2007 | Arnin et al. |
| 2007/0191947 A1 | 8/2007 | Arnin et al. |
| 2007/0191948 A1 | 8/2007 | Arnin et al. |
| 2007/0191949 A1 | 8/2007 | Arnin et al. |
| 2007/0191950 A1 | 8/2007 | Arnin et al. |
| 2007/0203490 A1 | 8/2007 | Zucherman et al. |
| 2007/0203491 A1 | 8/2007 | Pasquet et al. |
| 2007/0203493 A1 | 8/2007 | Zucherman et al. |
| 2007/0203494 A1 | 8/2007 | Arnin et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208347 A1 | 9/2007 | Zucherman et al. |
| 2007/0213724 A1 | 9/2007 | Arnin et al. |
| 2007/0213829 A1 | 9/2007 | Le Couedic et al. |
| 2007/0219552 A1 | 9/2007 | Zucherman et al. |
| 2007/0225706 A1 | 9/2007 | Clark et al. |
| 2007/0225724 A1 * | 9/2007 | Edmond .................. 606/90 |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233088 A1 | 10/2007 | Edmond |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0270812 A1 | 11/2007 | Peckham |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270840 A1 | 11/2007 | Chin et al. |
| 2007/0270968 A1 | 11/2007 | Baynham et al. |
| 2007/0272259 A1 | 11/2007 | Allard et al. |
| 2007/0276368 A1 | 11/2007 | Trieu et al. |
| 2007/0276370 A1 | 11/2007 | Altarac et al. |
| 2007/0276372 A1 | 11/2007 | Malandain et al. |
| 2007/0276373 A1 | 11/2007 | Malandain |
| 2007/0276381 A1 | 11/2007 | Butler et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2007/0282340 A1 | 12/2007 | Malandain |
| 2007/0282442 A1 | 12/2007 | Malandain et al. |
| 2007/0282443 A1 | 12/2007 | Globerman et al. |
| 2007/0288006 A1 | 12/2007 | Arnin et al. |
| 2007/0299526 A1 | 12/2007 | Malandain |
| 2008/0004706 A1 | 1/2008 | Arnin et al. |
| 2008/0009947 A1 | 1/2008 | Arnin et al. |
| 2008/0009948 A1 | 1/2008 | Arnin et al. |
| 2008/0015693 A1 | 1/2008 | Le Couedic |
| 2008/0015700 A1 | 1/2008 | Zucherman et al. |
| 2008/0015809 A1 | 1/2008 | Alumbaugh et al. |
| 2008/0021460 A1 | 1/2008 | Bruneau et al. |
| 2008/0021471 A1 | 1/2008 | Winslow et al. |
| 2008/0021488 A1 | 1/2008 | Berberich |
| 2008/0021560 A1 | 1/2008 | Zucherman et al. |
| 2008/0021561 A1 | 1/2008 | Zucherman et al. |
| 2008/0027433 A1 | 1/2008 | Kohm et al. |
| 2008/0027434 A1 | 1/2008 | Zucherman et al. |
| 2008/0027435 A1 | 1/2008 | Zucherman et al. |
| 2008/0027438 A1 | 1/2008 | Abdou |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033552 A1 | 2/2008 | Lee |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0033560 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039944 A1 | 2/2008 | Malandain et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051891 A1 | 2/2008 | Malandain et al. |
| 2008/0051892 A1 | 2/2008 | Malandain et al. |

(56) References Cited

U.S. PATENT DOCUMENTS

| | | |
|---|---|---|
| 2008/0051893 A1 | 2/2008 | Malandain et al. |
| 2008/0051894 A1 | 2/2008 | Malandain et al. |
| 2008/0051895 A1 | 2/2008 | Malandain et al. |
| 2008/0051896 A1 | 2/2008 | Suddaby |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0051906 A1 | 2/2008 | Malandain et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058934 A1 | 3/2008 | Malandain et al. |
| 2008/0058935 A1 | 3/2008 | Malandain et al. |
| 2008/0058936 A1 | 3/2008 | Malandain et al. |
| 2008/0058937 A1 | 3/2008 | Malandain et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071376 A1 | 3/2008 | Kohm et al. |
| 2008/0071378 A1 | 3/2008 | Zucherman et al. |
| 2008/0071380 A1 | 3/2008 | Sweeney |
| 2008/0082118 A1 | 4/2008 | Edidin et al. |
| 2008/0082167 A1 | 4/2008 | Edidin et al. |
| 2008/0082172 A1 | 4/2008 | Jackson |
| 2008/0086212 A1 | 4/2008 | Zucherman et al. |
| 2008/0108990 A1 | 5/2008 | Mitchell et al. |
| 2008/0109082 A1 | 5/2008 | Fink et al. |
| 2008/0114358 A1 | 5/2008 | Anderson et al. |
| 2008/0114455 A1 | 5/2008 | Lange et al. |
| 2008/0114456 A1 | 5/2008 | Dewey et al. |
| 2008/0132952 A1 | 6/2008 | Malandain et al. |
| 2008/0140125 A1 | 6/2008 | Mitchell et al. |
| 2008/0140207 A1 | 6/2008 | Olmos et al. |
| 2008/0147190 A1 | 6/2008 | Dewey et al. |
| 2008/0147192 A1 | 6/2008 | Edidin et al. |
| 2008/0161822 A1 | 7/2008 | Perez-Cruet et al. |
| 2008/0161856 A1 | 7/2008 | Liu et al. |
| 2008/0167655 A1 | 7/2008 | Wang et al. |
| 2008/0167656 A1 | 7/2008 | Zucherman et al. |
| 2008/0167657 A1 | 7/2008 | Greenhalgh |
| 2008/0172057 A1 | 7/2008 | Zucherman et al. |
| 2008/0177271 A1 | 7/2008 | Yeh |
| 2008/0177272 A1 | 7/2008 | Zucherman et al. |
| 2008/0177298 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0177391 A1 | 7/2008 | Mitchell et al. |
| 2008/0183210 A1 | 7/2008 | Zucherman et al. |
| 2008/0183211 A1* | 7/2008 | Lamborne et al. .......... 606/249 |
| 2008/0183218 A1* | 7/2008 | Mueller ............ A61B 17/7068 606/280 |
| 2008/0195152 A1 | 8/2008 | Altarac et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1* | 9/2008 | Trautwein .......... A61B 17/1671 606/301 |
| 2008/0234733 A1 | 9/2008 | Scrantz et al. |
| 2008/0234735 A1 | 9/2008 | Joshi |
| 2008/0234824 A1 | 9/2008 | Youssef et al. |
| 2008/0243186 A1 | 10/2008 | Abdou |
| 2008/0243250 A1 | 10/2008 | Seifert et al. |
| 2008/0249528 A1 | 10/2008 | Khalife |
| 2008/0249569 A1 | 10/2008 | Waugh et al. |
| 2008/0249622 A1 | 10/2008 | Gray |
| 2008/0255616 A1 | 10/2008 | Atkinson et al. |
| 2008/0255668 A1 | 10/2008 | Fallin et al. |
| 2008/0255669 A1 | 10/2008 | Fallin et al. |
| 2008/0262617 A1 | 10/2008 | Froehlich et al. |
| 2008/0262619 A1 | 10/2008 | Ray |
| 2008/0269904 A1 | 10/2008 | Voorhies |
| 2008/0281359 A1 | 11/2008 | Abdou |
| 2008/0281360 A1 | 11/2008 | Vittur et al. |
| 2008/0281361 A1 | 11/2008 | Vittur et al. |
| 2008/0281423 A1 | 11/2008 | Sheffer et al. |
| 2008/0287997 A1 | 11/2008 | Altarac et al. |
| 2008/0288072 A1 | 11/2008 | Kohm |
| 2008/0288075 A1 | 11/2008 | Zucherman et al. |
| 2008/0288078 A1 | 11/2008 | Kohm et al. |
| 2008/0294199 A1 | 11/2008 | Kohm et al. |
| 2008/0294200 A1 | 11/2008 | Kohm et al. |
| 2008/0294204 A1 | 11/2008 | Chirico et al. |
| 2008/0294263 A1 | 11/2008 | Altarac et al. |
| 2008/0300686 A1 | 12/2008 | Khoo |
| 2008/0300687 A1 | 12/2008 | Lin et al. |
| 2008/0312741 A1 | 12/2008 | Lee et al. |
| 2008/0319549 A1 | 12/2008 | Greenhalgh et al. |
| 2008/0319550 A1 | 12/2008 | Altarac et al. |
| 2009/0005819 A1 | 1/2009 | Ben-Mokhtar et al. |
| 2009/0005873 A1 | 1/2009 | Slivka et al. |
| 2009/0012528 A1 | 1/2009 | Aschmann et al. |
| 2009/0012614 A1 | 1/2009 | Dixon |
| 2009/0018658 A1 | 1/2009 | Garcia |
| 2009/0018662 A1 | 1/2009 | Pasquet et al. |
| 2009/0030523 A1 | 1/2009 | Taylor |
| 2009/0036925 A1 | 2/2009 | Sala et al. |
| 2009/0043342 A1 | 2/2009 | Freedland |
| 2009/0054931 A1 | 2/2009 | Metz-Stavenhagen |
| 2009/0054988 A1 | 2/2009 | Hess |
| 2009/0062915 A1 | 3/2009 | Kohm et al. |
| 2009/0062918 A1 | 3/2009 | Wang et al. |
| 2009/0082808 A1 | 3/2009 | Butler et al. |
| 2009/0093817 A1 | 4/2009 | Zucherman et al. |
| 2009/0093843 A1 | 4/2009 | Lemoine et al. |
| 2009/0093883 A1 | 4/2009 | Carrasco |
| 2009/0099603 A1 | 4/2009 | Nishida |
| 2009/0105761 A1 | 4/2009 | Robie |
| 2009/0105773 A1 | 4/2009 | Lange et al. |
| 2009/0112266 A1 | 4/2009 | Weng et al. |
| 2009/0118833 A1 | 5/2009 | Hudgins et al. |
| 2009/0138045 A1 | 5/2009 | Ciupik et al. |
| 2009/0138046 A1 | 5/2009 | Altarac et al. |
| 2009/0138087 A1 | 5/2009 | Miglietta et al. |
| 2009/0149885 A1 | 6/2009 | Durward et al. |
| 2009/0149886 A1 | 6/2009 | Zentes et al. |
| 2009/0171399 A1 | 7/2009 | White et al. |
| 2009/0198241 A1 | 8/2009 | Phan |
| 2009/0198277 A1 | 8/2009 | Gordon et al. |
| 2009/0198278 A1 | 8/2009 | Shibata et al. |
| 2009/0198337 A1 | 8/2009 | Phan |
| 2009/0198338 A1 | 8/2009 | Phan |
| 2009/0209965 A1 | 8/2009 | Lewis |
| 2009/0216274 A1 | 8/2009 | Morancy-Meister et al. |
| 2009/0222043 A1 | 9/2009 | Altarac et al. |
| 2009/0234389 A1 | 9/2009 | Chuang et al. |
| 2009/0240280 A1 | 9/2009 | Wang et al. |
| 2009/0240283 A1 | 9/2009 | Carls et al. |
| 2009/0248076 A1 | 10/2009 | Reynolds et al. |
| 2009/0248079 A1 | 10/2009 | Kwak et al. |
| 2009/0248081 A1 | 10/2009 | LeHuec et al. |
| 2009/0254122 A1 | 10/2009 | Khalife |
| 2009/0254185 A1 | 10/2009 | Dollinger |
| 2009/0259316 A1 | 10/2009 | Ginn et al. |
| 2009/0265006 A1 | 10/2009 | Seifert et al. |
| 2009/0270919 A1 | 10/2009 | Dos Reis, Jr. |
| 2009/0275982 A1 | 11/2009 | Taylor |
| 2009/0281626 A1 | 11/2009 | Farr |
| 2009/0292314 A1 | 11/2009 | Mangione et al. |
| 2009/0292315 A1 | 11/2009 | Trieu |
| 2009/0292316 A1 | 11/2009 | Hess |
| 2009/0292317 A1 | 11/2009 | Belliard |
| 2009/0297603 A1 | 12/2009 | Joshi |
| 2009/0306715 A1 | 12/2009 | Jackson et al. |
| 2009/0306716 A1 | 12/2009 | Beger et al. |
| 2009/0318967 A1 | 12/2009 | Jeon et al. |
| 2009/0326581 A1 | 12/2009 | Galley et al. |
| 2010/0004688 A1 | 1/2010 | Maas et al. |
| 2010/0004744 A1 | 1/2010 | Zucherman et al. |
| 2010/0010546 A1 | 1/2010 | Hermida Ochoa |
| 2010/0010548 A1 | 1/2010 | Hermida Ochoa |

(56) References Cited

U.S. PATENT DOCUMENTS

| | | | |
|---|---|---|---|
| 2010/0036419 A1 | 2/2010 | Patel et al. | |
| 2010/0174373 A1 | 7/2010 | Galley et al. | |
| 2010/0191287 A1 | 7/2010 | Bucci | |
| 2010/0211101 A1 | 8/2010 | Blackwell et al. | |
| 2010/0222817 A1 | 9/2010 | Perez-Cruet et al. | |
| 2010/0241167 A1 | 9/2010 | Taber et al. | |
| 2011/0029020 A1 | 2/2011 | Gordon et al. | |
| 2011/0054531 A1 | 3/2011 | Lamborne et al. | |
| 2011/0066186 A1 | 3/2011 | Boyer, II et al. | |
| 2011/0144692 A1 | 6/2011 | Saladin et al. | |
| 2011/0160772 A1* | 6/2011 | Arcenio et al. | 606/248 |
| 2011/0166600 A1 | 7/2011 | Lamborne et al. | |
| 2011/0172709 A1* | 7/2011 | Lyons et al. | 606/249 |
| 2011/0172711 A1 | 7/2011 | Kirschman | |
| 2011/0172720 A1* | 7/2011 | Metcalf et al. | 606/324 |
| 2011/0190816 A1 | 8/2011 | Sheffer et al. | |
| 2011/0264221 A1 | 10/2011 | Woodward et al. | |
| 2011/0313458 A1 | 12/2011 | Butler et al. | |
| 2011/0319936 A1 | 12/2011 | Gordon et al. | |
| 2012/0016418 A1 | 1/2012 | Chin et al. | |
| 2012/0089184 A1* | 4/2012 | Yeh | A61B 17/7068 606/248 |
| 2012/0109203 A1* | 5/2012 | Dryer et al. | 606/249 |
| 2012/0221050 A1* | 8/2012 | Ingalhalikar et al. | 606/248 |
| 2012/0232592 A1* | 9/2012 | Massoudi | A61B 17/7068 606/279 |
| 2013/0012996 A1 | 1/2013 | Zamani et al. | |
| 2014/0243898 A1* | 8/2014 | Fessler | 606/249 |
| 2014/0343608 A1* | 11/2014 | Whiton et al. | 606/249 |
| 2015/0351813 A1 | 12/2015 | Lamborne et al. | |
| 2016/0113687 A1 | 4/2016 | Taber et al. | |
| 2016/0120579 A1 | 5/2016 | Lamborne et al. | |
| 2017/0189078 A1 | 7/2017 | Lamborne et al. | |

FOREIGN PATENT DOCUMENTS

| | | |
|---|---|---|
| JP | H0737112 U | 7/1995 |
| JP | 2003220071 A | 8/2003 |
| JP | 2003523214 A | 8/2003 |
| JP | 2005525907 A | 9/2005 |
| JP | 2008539819 A | 11/2008 |
| KR | 20060124851 A | 12/2006 |
| WO | WO 1994/000062 | 1/1994 |
| WO | WO 2003/099147 | 12/2003 |
| WO | WO 2004/039239 | 5/2004 |
| WO | WO 2004/105656 | 12/2004 |
| WO | WO 2005/009300 | 2/2005 |
| WO | WO 2005/055868 | 6/2005 |
| WO | WO 2006/102269 | 9/2006 |
| WO | WO 2006/119235 | 11/2006 |
| WO | WO 2007/019391 | 2/2007 |
| WO | WO 2008/067452 | 6/2008 |
| WO | WO 2008/086533 | 7/2008 |
| WO | WO 2008/088613 | 7/2008 |
| WO | WO 2008/124831 | 10/2008 |
| WO | WO 2009/058439 | 5/2009 |
| WO | WO 2011/019756 | 2/2011 |
| WO | WO 2011/019758 | 2/2011 |

OTHER PUBLICATIONS

"Australian Application Serial No. 2007343630, Notice of Acceptance dated Dec. 2, 2013", 2 pgs.
"Australian Application Serial No. 2008204769, Non-Final Office Action dated Jun. 28, 2012", 3 pgs.
"Australian Application serial No. 2008319176, First Examiner Report dated Mar. 19, 2013", 4 pgs.
"Australian Application Serial No. 2008319176, Voluntary Amendment dated May 31, 2010", 24 pgs.
"European Application Serial No. 07854667.8, Communication Pursuant to Article 94(3) EPC dated Jul. 2, 2015", 4 pgs.
"European Application Serial No. 07854667.8, Communication Pursuant to Article 94(3) EPC dated Mar. 10, 2017", 4 pgs.
"European Application Serial No. 07854667.8, Extended European Search Report dated Mar. 12, 2012", 10 pgs.
"European Application Serial No. 07854667.8, Response filed Jul. 17, 2017 to Communication Pursuant to Article 94(3) EPC dated Mar. 10, 2017", 16 pgs.
"European Application Serial No. 07854667.8, Response filed Oct. 8, 2012 to Extended European Search Report dated Mar. 12, 2012", 17 pgs.
"European Application Serial No. 08727627.5, Extended European Search Report dated Mar. 12, 2012", 5 pgs.
"European Application Serial No. 08727627.5, Resposne filed Oct. 8, 2012 to Extended European Search Report dated Mar. 12, 2012", 15 pgs.
"European Application Serial No. 10759359.2, Extended European Search Report dated Nov. 26, 2013", 5 pgs.
"European Application Serial No. 10808656.2, Extended European Search Report dated Jul. 7, 2014", 7 pgs.
"European Application Serial No. 10808656.2, Office Action dated Jun. 20, 2017", 5 pgs.
"European Application Serial No. 10808656.2, Response filed Jan. 23, 2015 to Extended European Search Report dated May 12, 2011", 14 pgs.
"European Application Serial No. 10808656.2, Response filed Oct. 30, 2017 to Office Action dated Jun. 20, 2017", 10 pgs.
"European Application Serial No. 13180855.2, Decision to grant dated Dec. 17, 2015", 2 pgs.
"European Application Serial No. 13180855.2, Extended European Search Report dated Oct. 7, 2013", 4 pgs.
"European Application Serial No. 13180855.2, Office Action dated Jul. 23, 2015", 45 pgs.
"European Application Serial No. 13180855.2, Response filed May 27, 2014 to Extended European Search Report dated Oct. 7, 2013", 17 pgs.
"International Application Serial No. PCT/US2005/038489, International Preliminary Report on Patentability dated May 1, 2007", 6 pgs.
"International Application Serial No. PCT/US2007/084856, International Preliminary Report on Patentability dated Jul. 14, 2009", 9 pgs.
"International Application Serial No. PCT/US2007/084856, International Search Report dated Dec. 10, 2008", 2 pgs.
"International Application Serial No. PCT/US2007/084856, Written Opinion dated Dec. 10, 2008", 8 pgs.
"International Application Serial No. PCT/US2008/050931, International Preliminary Report on Patentability dated Mar. 19, 2010", 3 pgs.
"International Application Serial No. PCT/US2008/050931, International Search Report dated Jul. 28, 2008", 1 pg.
"International Application Serial No. PCT/US2008/050931, Written Opinion dated Jul. 28, 2008", 3 pgs.
"International Application Serial No. PCT/US2008/070353, International Preliminary Report on Patentability dated Apr. 5, 2010", 10 pgs.
"International Application Serial No. PCT/US2008/070353, International Search Report and Written Opinion dated Nov. 10, 2008", 11 pgs.
"International Application Serial No. PCT/US2010/045079, International Preliminary Report on Patentability dated Feb. 14, 2012", 4 pgs.
"International Application Serial No. PCT/US2010/045079, International Search Report dated Apr. 22, 2011", 9 pgs.
"International Application Serial No. PCT/US2010/045079, Written Opinion dated Apr. 22, 2011", 3 pgs.
"International Application Serial No. PCT/US2010/045081, International Preliminary report on Patentability dated Feb. 14, 2012", 4 pgs.
"International Application Serial No. PCT/US2010/045081, International Search Report dated Apr. 22, 2011", 9 pgs.
"International Application Serial No. PCT/US2010/045081, Written Opinion dated Apr. 22, 2011", 3 pgs.
"U.S. Appl. No. 11/934,604, Applicant's Summary of Examiner Interview dated Sep. 12, 2011", 1 pgs.

(56) References Cited

OTHER PUBLICATIONS

"U.S. Appl. No. 11/934,604, Examiner Interview Summary dated Feb. 27, 2012", 3 pgs.
"U.S. Appl. No. 11/934,604, Examiner Interview Summary dated Sep. 1, 2011", 3 pgs.
"U.S. Appl. No. 11/934,604, Final Office Action dated Apr. 24, 2012", 39 pgs.
"U.S. Appl. No. 11/934,604, Non-Final Office Action dated Apr. 13, 2011", 33 pgs.
"U.S. Appl. No. 11/934,604, Non-Final Office Action dated Oct. 19, 2011", 41 pgs.
"U.S. Appl. No. 11/934,604, Notice of Allowance dated Jun. 19, 2012", 10 pgs.
"U.S. Appl. No. 11/934,604, Notice of Non-Compliant Amendment dated Feb. 3, 2012", 2 pgs.
"U.S. Appl. No. 11/934,604, Preliminary Amendment dated Mar. 4, 2011", 11 pgs.
"U.S. Appl. No. 11/934,604, Response filed Feb. 21, 2012 to Non-Final Office Action dated Oct. 19, 2011", 37 pgs.
"U.S. Appl. No. 11/934,604, Response filed Jul. 13, 2013 to Non-Final Office Action dated Apr. 13, 2011", 28 pgs.
"U.S. Appl. No. 11/934,604, Response filed Mar. 22, 2011 to Restriction Requirement dated Feb. 24, 2011", 1 pgs.
"U.S. Appl. No. 11/934,604, Response filed May 21, 2012 to Final Office Action dated Apr. 24, 2012", 13 pgs.
"U.S. Appl. No. 11/934,604, Restriction Requirement dated Feb. 24, 2011", 12 pgs.
"U.S. Appl. No. 12/020,282, Final Office Action dated Dec. 5, 2014", 18 pgs.
"U.S. Appl. No. 12/020,282, Final Office Action dated May 11, 2012", 35 pgs.
"U.S. Appl. No. 12/020,282, Non-Final Office Action dated Apr. 17, 2014", 34 pgs.
"U.S. Appl. No. 12/020,282, Non-Final Office Action dated Nov. 23, 2011", 11 pgs.
"U.S. Appl. No. 12/020,282, Notice of Allowance dated Feb. 12, 2015", 9 pgs.
"U.S. Appl. No. 12/020,282, Restriction Requirement dated Jul. 14, 2011", 7 pgs.
"U.S. Appl. No. 12/538,710, Non-Final Office Action dated Feb. 6, 2012", 71 pgs.
"U.S. Appl. No. 12/538,710, Notice of Allowance dated Nov. 16, 2012", 15 pgs.
"U.S. Appl. No. 12/538,710, Restriction Requirement dated Nov. 9, 2011", 12 pgs.
"U.S. Appl. No. 12/751,856, Final Office Action dated Jun. 17, 2015", 26 pgs.
"U.S. Appl. No. 12/751,856, Final Office Action dated May 11, 2012", 43 pgs.
"U.S. Appl. No. 12/751,856, Non-Final Office Action dated Apr. 22, 2014", 45 pgs.
"U.S. Appl. No. 12/751,856, Non-Final Office Action dated Oct. 28, 2011", 10 pgs.
"U.S. Appl. No. 12/751,856, Non-Final Office Action dated Dec. 29, 2014", 36 pgs.
"U.S. Appl. No. 12/751,856, Notice of Allowance dated Sep. 28, 2015", 5 pgs.
"U.S. Appl. No. 12/854,125, Final Office Action dated Apr. 24, 2012", 43 pgs.
"U.S. Appl. No. 12/854,125, Final Office Action dated Dec. 31, 2014", 52 pgs.
"U.S. Appl. No. 12/854,125, Non-Final Office Action dated Jun. 26, 2014", 41 pgs.
"U.S. Appl. No. 12/854,125, Non-Final Office Action dated Oct. 31, 2011", 9 pgs.
"U.S. Appl. No. 12/854,125, Notice of Allowance dated Oct. 7, 2015", 9 pgs.
"U.S. Appl. No. 13/460,738, Final Office Action dated Apr. 3, 2013", 33 pgs.
"U.S. Appl. No. 13/460,738, Non-Final Office Action dated Jul. 27, 2012", 33 pgs.
"U.S. Appl. No. 14/739,170, Non-Final Office Action dated Jul. 14, 2016", 13 pgs.
"U.S. Appl. No. 14/739,170, Notice of Allowance dated Jun. 13, 2017", 8 pgs.
"U.S. Appl. No. 14/739,170, Notice of Allowance dated Nov. 23, 2016", 13 pgs.
"U.S. Appl. No. 14/739,170, Restriction Requirement dated Apr. 5, 2016", 6 pgs.
"U.S. Appl. No. 14/980,982, Corrected Notice of Allowance dated May 2, 2017", 5 pgs.
"U.S. Appl. No. 14/980,982, Non-Final Office Action dated Nov. 18, 2016", 16 pgs.
"U.S. Appl. No. 14/980,982, Notice of Allowance dated Apr. 4, 2017", 10 pgs.
"U.S. Appl. No. 14/980,982, Restriction Requirement dated Apr. 7, 2016", 6 pgs.
"U.S. Appl. No. 14/992,323, Non-Final Office Action dated Apr. 7, 2016", 15 pgs.
"U.S. Appl. No. 14/992,323, Notice of Allowance dated Apr. 5, 2017", 8 pgs.
"U.S. Appl. No. 14/992,323, Notice of Allowance dated Dec. 22, 2016", 9 pgs.
"U.S. Appl. No. 14/992,323, Notice of Allowance dated Sep. 7, 2016", 9 pgs.
Bostman, et al., "Posterior Spinal Fusion Using Internal Fixation with the Daab Plate", (1984), 310-314.
Lee, et al., "An Interspinous Process Distractor (X Stop) for Lumbar Spinal Stenosis in Elderly Patients", J. Spinal Discord Tech., vol. 17, No. 1, (Feb. 2004), 72-77.

\* cited by examiner

SPINAL FIXATION DEVICE

RELATED APPLICATIONS

This application claims priority to U.S. Provisional Patent Application No. 61/544,920, filed 7 Oct. 2011, and to U.S. Provisional Patent Application No. 61/558,736, filed 11 Nov. 2011, both of which are incorporated herein by reference.

BACKGROUND

Spinal fixation is a neurosurgical procedure in which two or more vertebrae are anchored to each other using a synthetic device. Spinal fixation is often performed to stabilize the spine or reduce vertebral mobility, and thus reduce pain, tingling in the extremities due to compression of nerves, and/or to avoid potential damage to the spinal column.

During spinal fixation surgery, bone is often shaved from spinous processes of vertebrae to be fixed, in order to provide an even surface for fixation plates or other devices. However, shaving thins the bone, thus compromising vertebral strength.

SUMMARY

The spinal fixation device described herein addresses the problem of bone loss due to spinous shaving, by providing plates that join together in plane, or with one or both of the plates tilted out of plane and/or rotated with respect to one another. The wide range of plate positions provided by the disclosed device allows a neurosurgeon to customize placement of the plates with a patient's existing bone topography, thereby reducing or eliminating the need to shave the spinous processes.

In one embodiment, a spinal fixation device includes a pair of substantially s-shaped plates, each having a plurality of apertures therethrough. A bolt having a head with a rounded or beveled base joins the plates at a desired orientation. The rounded or beveled base allows the plates to be joined while rotated or tilted with respect to one another and the spinal column.

DETAILED DESCRIPTION

Figure 1:
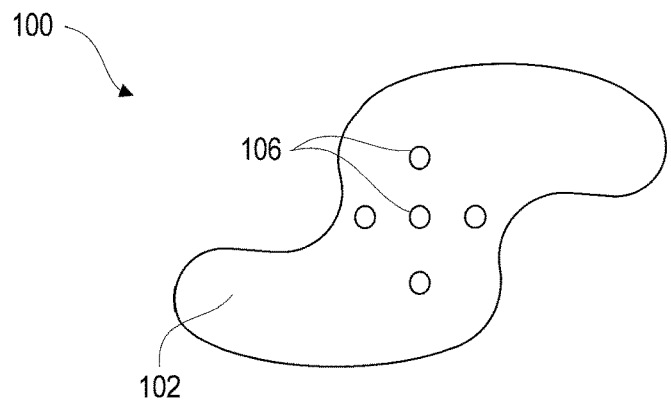
FIG. 1 is a front view of a spinal fixation device, according to an embodiment.
Figure 2:
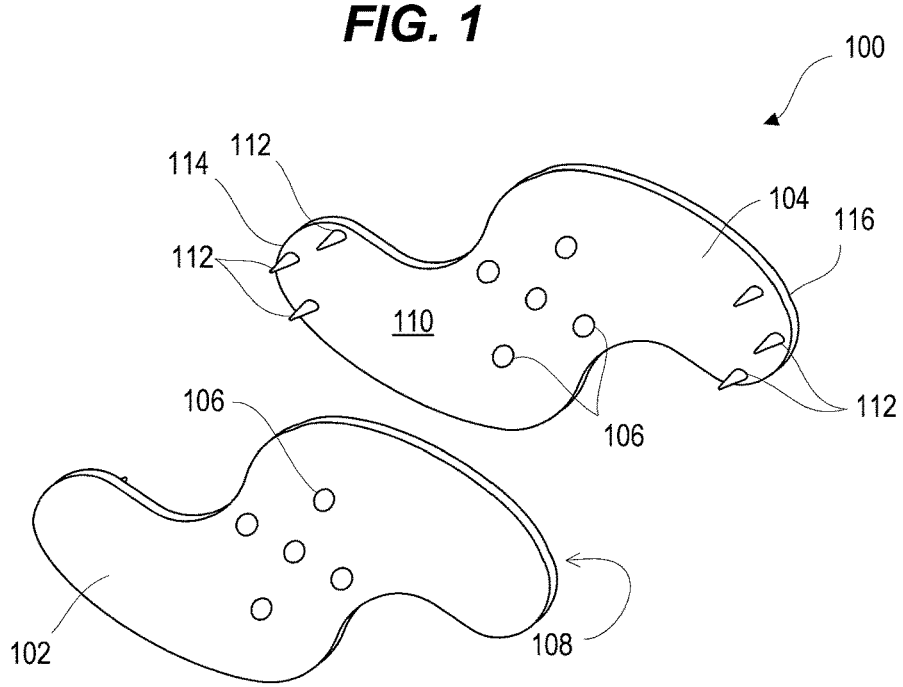
FIG. 2 is a perspective view showing dual plates of the spinal fixation device of FIG. 1.
Figure 3:
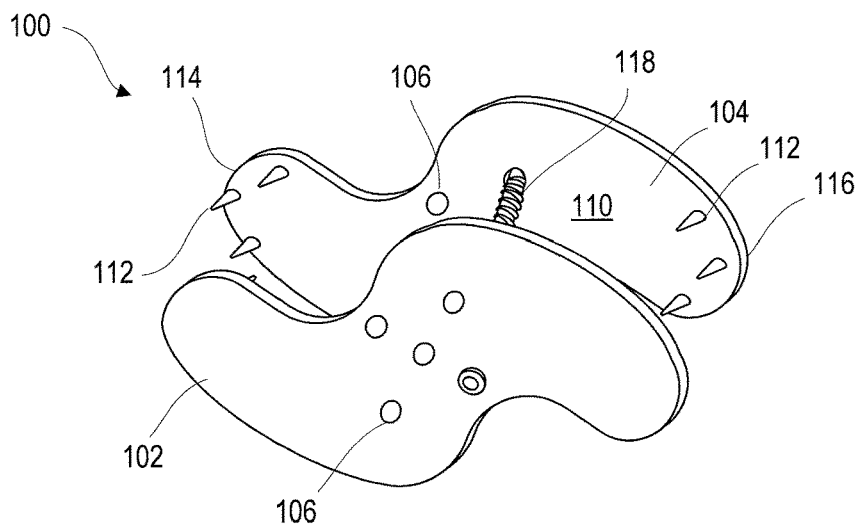
FIG. 3 is a perspective view of the device of FIGS. 1-2, showing a bolt joining a hole of the front plate with a non-analogous hole of the rear plate, according to an embodiment.
Figure 4:
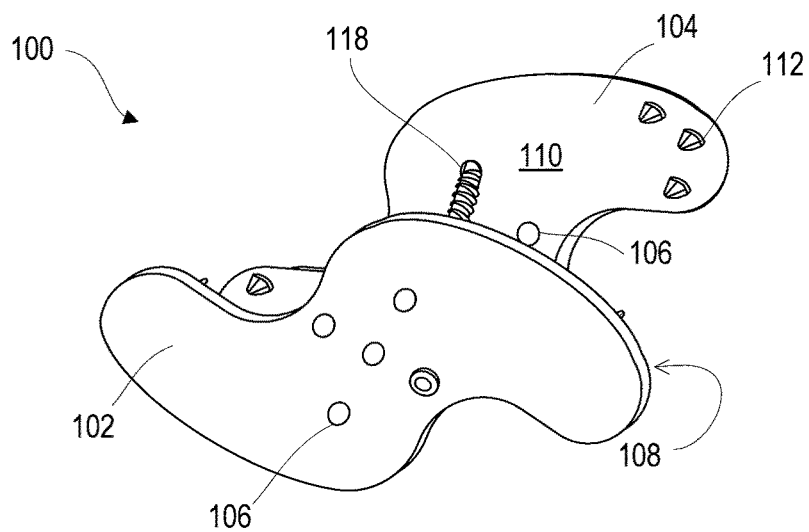
FIG. 4 is a cross-sectional view showing the plates of FIGS. 2-3 rotated with respect to one another and joined via a bolt through non-analogous holes of the front and rear plates, according to an embodiment.

FIGS. 1-4 show a spinal fixation device 100, and are best viewed together with the following description. Device 100 includes a front plate 102 and a rear plate 104, each having a plurality of apertures or holes 106 therethrough. Plates 102, 104 are for example titanium, although they may be formed with other biocompatible materials having sufficient strength to fuse adjacent vertebrae. Bone-contact surfaces 108 and 110 of plates 102 and 104, respectively, include one or more prongs 112. As shown, three prongs 112 are positioned with opposing arms 114, 116 of each plate. However, it will be appreciated that more or fewer prongs may be used, and that number and arrangement of prongs may differ from plate to plate (i.e., from plate 102 to plate 104), or from arm to arm (i.e., from arm 114 to arm 116). When plates 102, 104 are placed with bone (e.g., with spinous processes), prongs 112 penetrate or bite into the bone, to enhance fixation of device 100.

Figure 13:
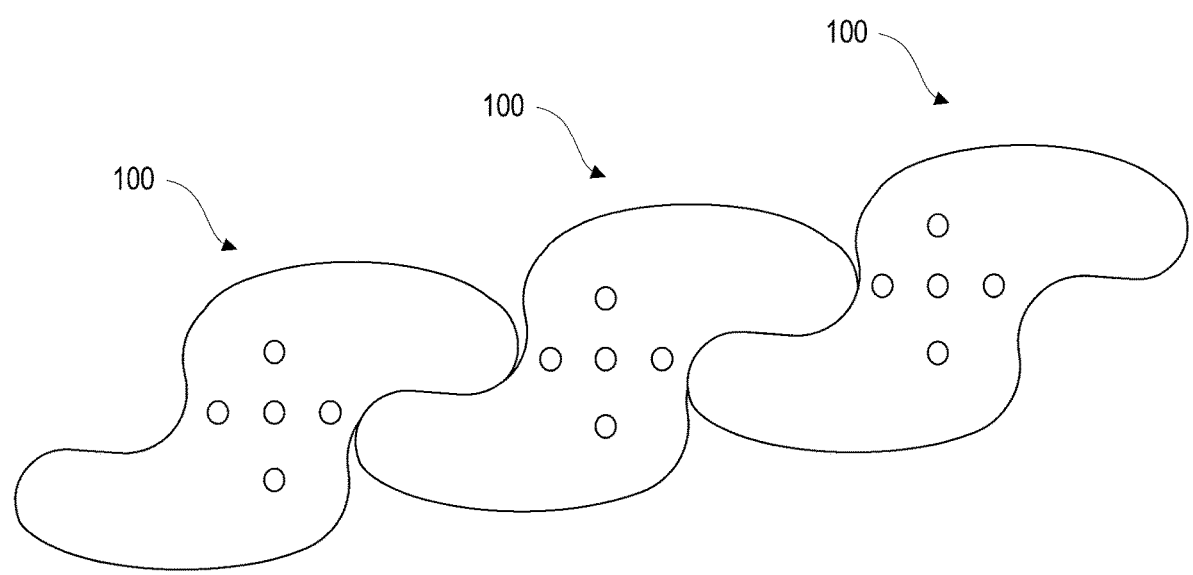
FIG. 13 shows three stacked spinal fixation devices, according to an embodiment.
Figure 14:
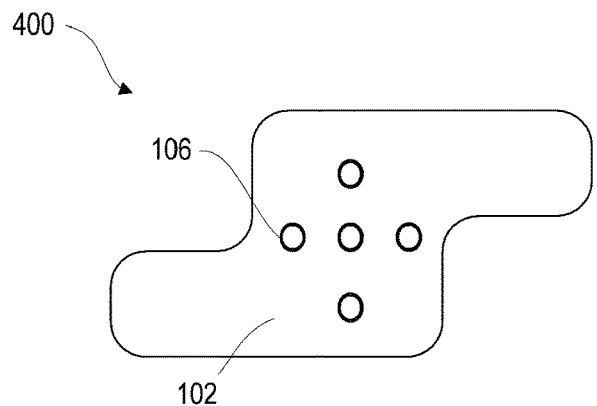
FIG. 14 is a front view of a spinal fixation device, according to an embodiment.
Figure 15:
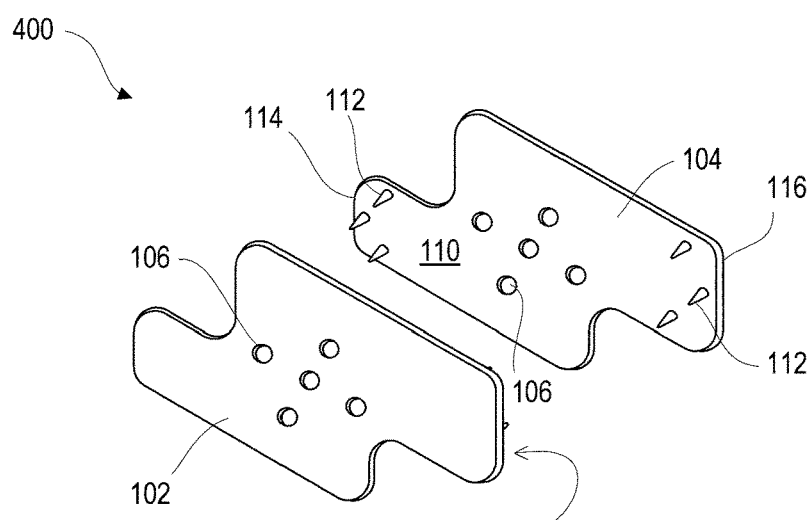
FIG. 15 is a perspective view showing dual plates of the spinal fixation device of FIG. 12.
Figure 16:
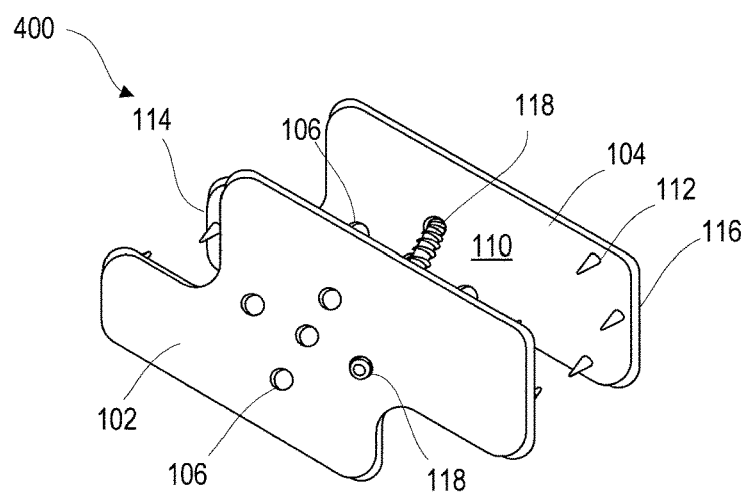
FIG. 16 is a perspective view of the device of FIGS. 14 and 15, showing a bolt joining a hole of the front plate with a non-analogous hole of the rear plate, according to an embodiment.
Figure 17:
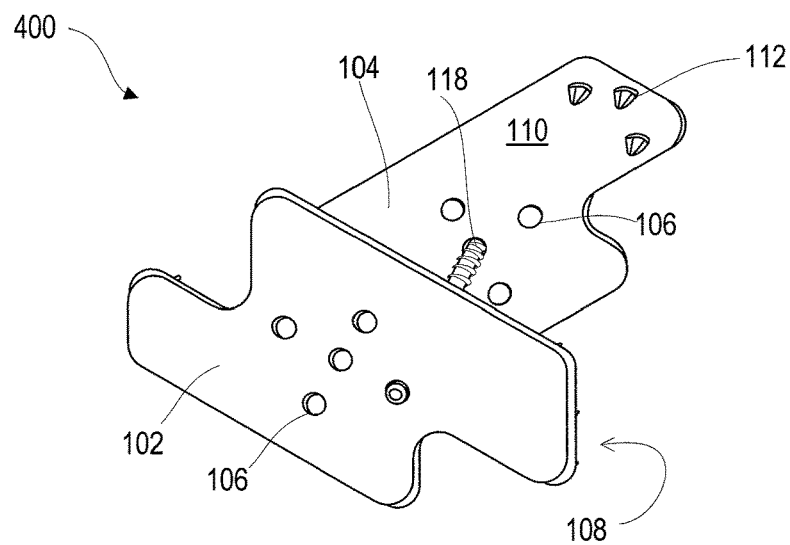
FIG. 17 shows plates of the spinal fixation device of FIGS. 14-16 joined while rotated and tilted with respect to one another.
Figure 18:
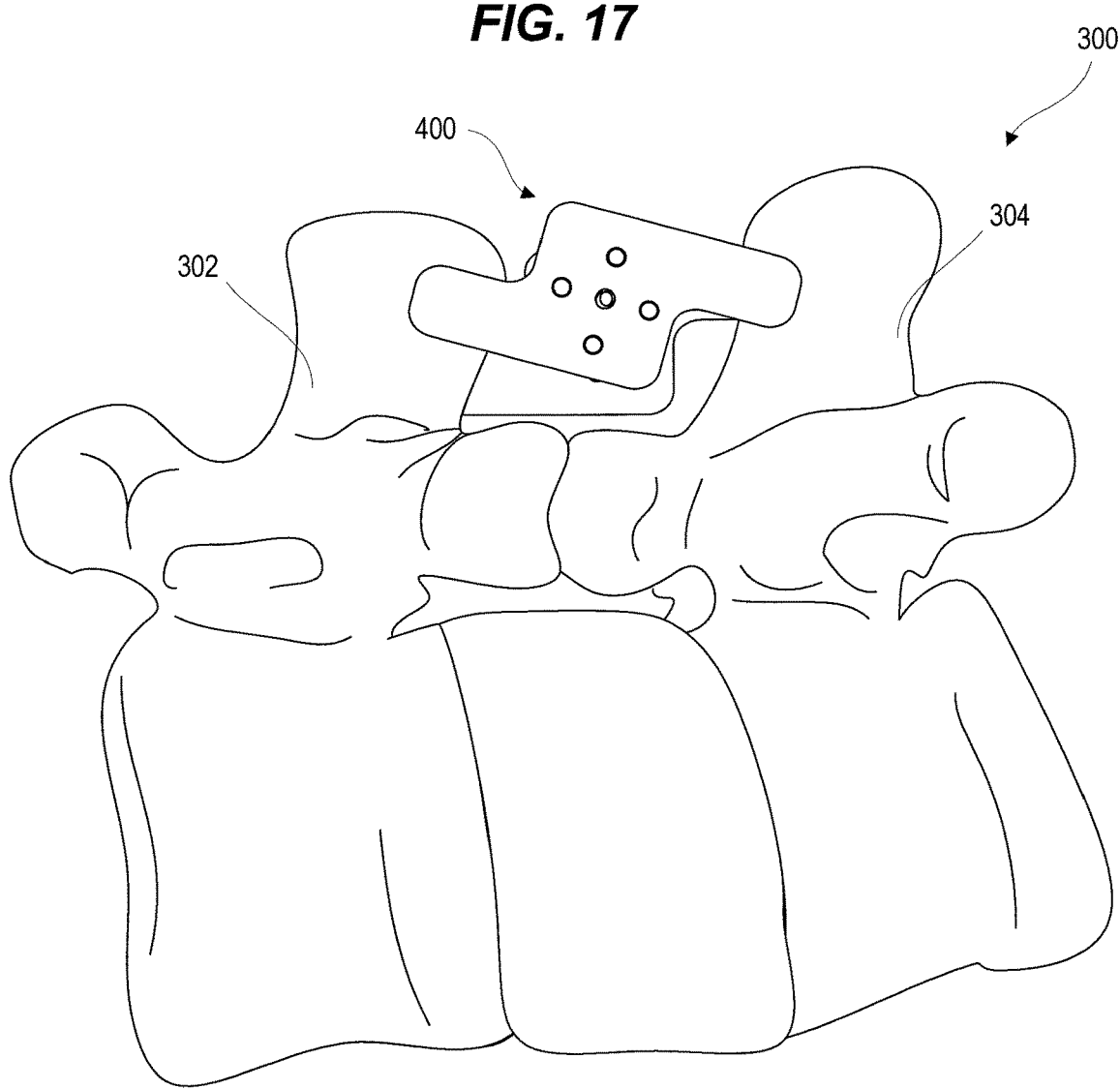
FIG. 18 shows the spinal fixation device of FIGS. 14-16 secured with and fusing adjacent vertebrae, according to an embodiment.

Plates 102, 104 may be generally s-shaped to facilitate stacking and side-by-side placement of multiple devices 100, in addition to providing opposing arms 114, 116 for prongs 112. See, for example, FIG. 13.

Figure 5:
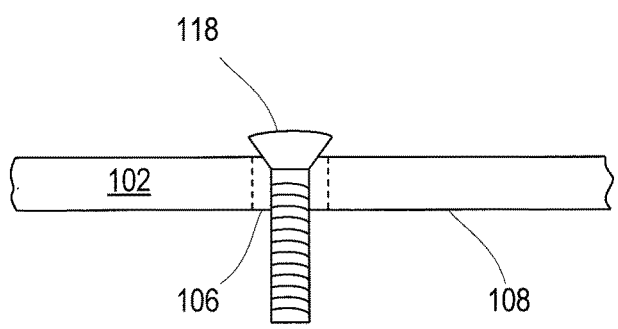
FIG. 5 is a cross-sectional view showing a bolt fitted with a hole of a spinal fixation device, according to an embodiment.
Figure 6:
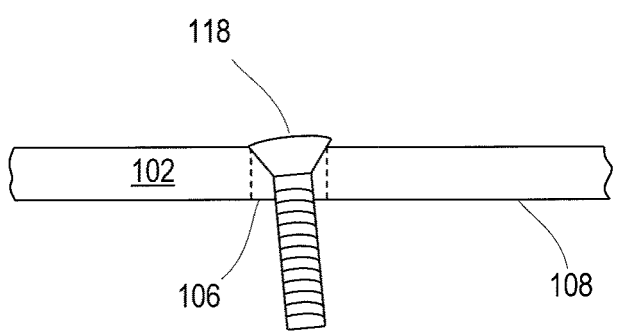
FIG. 6 shows the bolt of FIG. 5 tilted or rotated with respect to its hole.
Figure 7:
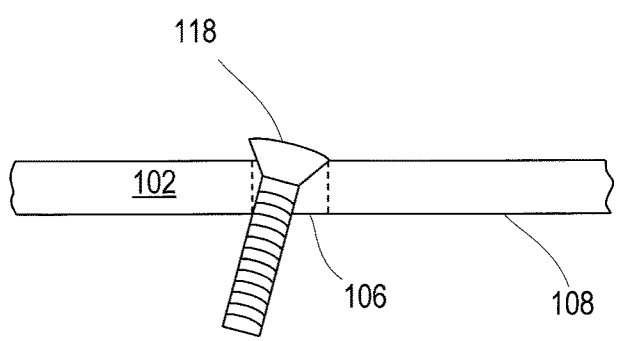
FIG. 7 shows the bolt of FIG. 5 tilted or rotated with respect to its hole.
Figure 8:
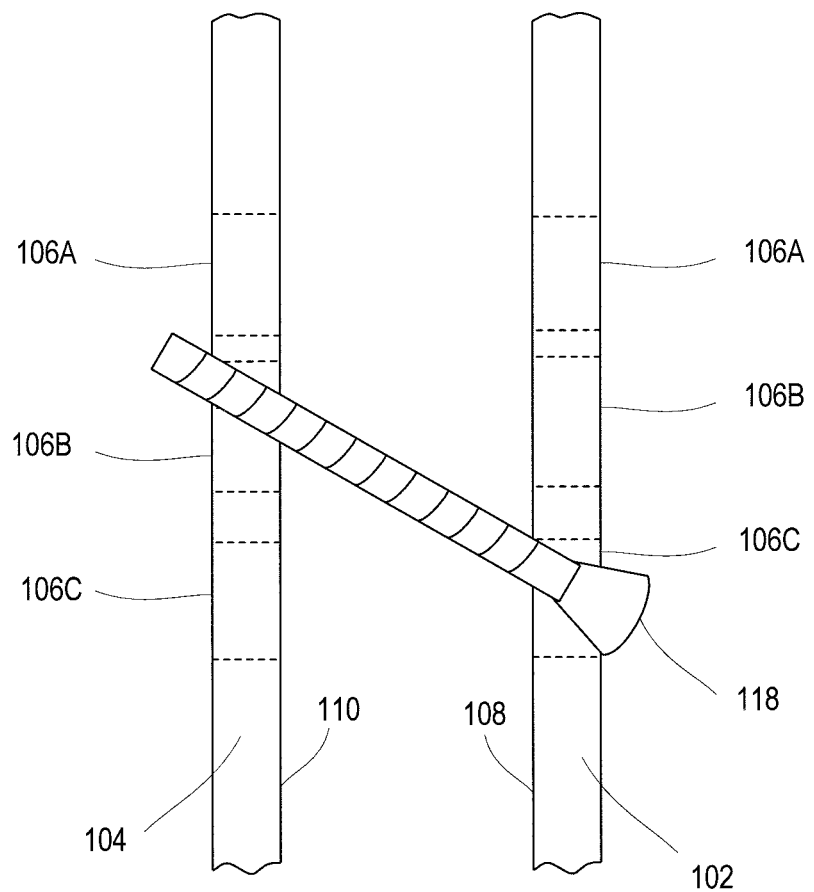
FIG. 8 is a cross-sectional side view illustrating male and female joining members for rotatably securing a bolt with plates of a spinal fixation device, according to an embodiment.

A bolt or screw (hereinafter, "bolt 118") joins plate 102 with plate 104. As shown in FIGS. 5-7, bolt 118 includes a tapered or rounded head, allowing bolt 118 to rotate and tilt within one hole 106. The angle of bolt 106 between plates 102 and 104 may therefore be varied such that bolt 106 may join non-analogous holes 106 of opposing plates 102 and 104, as schematically shown in FIG. 8. It will be appreciated that bolt 118 may also be a set bolt, blind bolts, ziptie bolt or other bolt. Bolt 118 may be secured with plates 102 and 104 using a nut.

Figure 9:
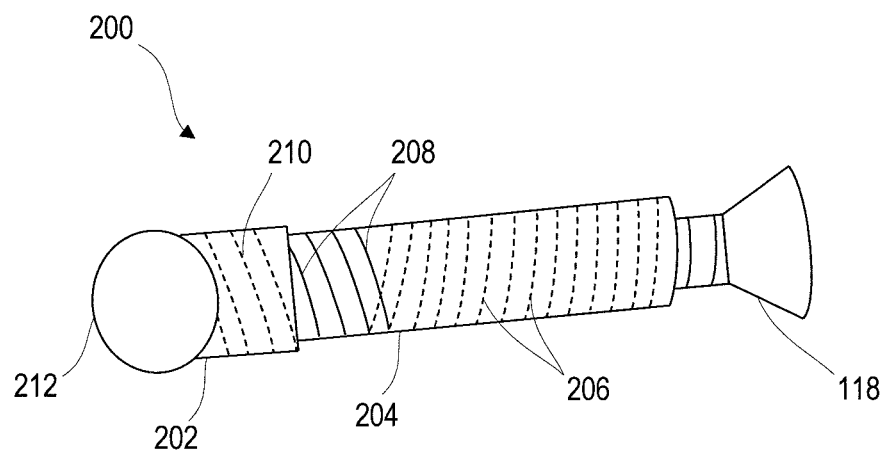
FIG. 9 shows a male and female connection system for securing a bolt with the spinal fixation device of FIGS. 1-4, according to an embodiment.
Figure 10:
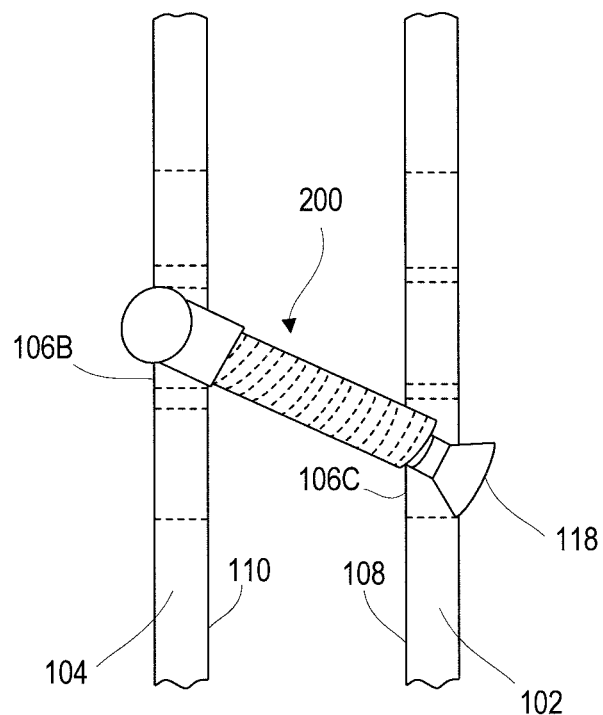
FIG. 10 shows the connection system and bolt of FIG. 9 connecting plates of the spinal fixation device of FIGS. 1-4, according to an embodiment.

A male and female connection system 200 may be used with bolt 118 and device 100. FIGS. 9 and 10 illustrate a system 200 including a ball-and-socket receiving portion 202 for accepting a bolt collar 204. Bolt collar 204 may include internal threads 206 (depicted in dotted outline) for mating with an externally threaded screw 118. Bolt collar 204 may also include external threads 208 for mating with internal threads 210 (also in dotted outline) of receiving portion 202.

A spherical or semi-spherical head 212 of ball-and-socket receiving portion 202 facilitates variable placement of screw 118 with holes 106, and may increase a range of possible angles between screw 118 and plates 102, 104. Head 212 may include an aperture or other surface feature (not shown) for temporarily joining with a hex key or other tool for tightening bolt 118 with system 200. An exemplary tool for tightening bolt 118 and/or system 200 may be an electric Allen wrench having internal actuators within the long stem of the Allen wrench for turning the key tip, without having to rotate the Allen wrench about the tip when the tip is mated with bolt 118. The electric Allen wrench may have a single long stem for mating with an electric drill, with the distal end of the stem (distal to the drill) configured to fit a variety of "key end" sizes. In one aspect, the key ends are tapered from a stem-connecting end to a narrower end for fitting with a bolt, such as bolt 118.

Figure 11:
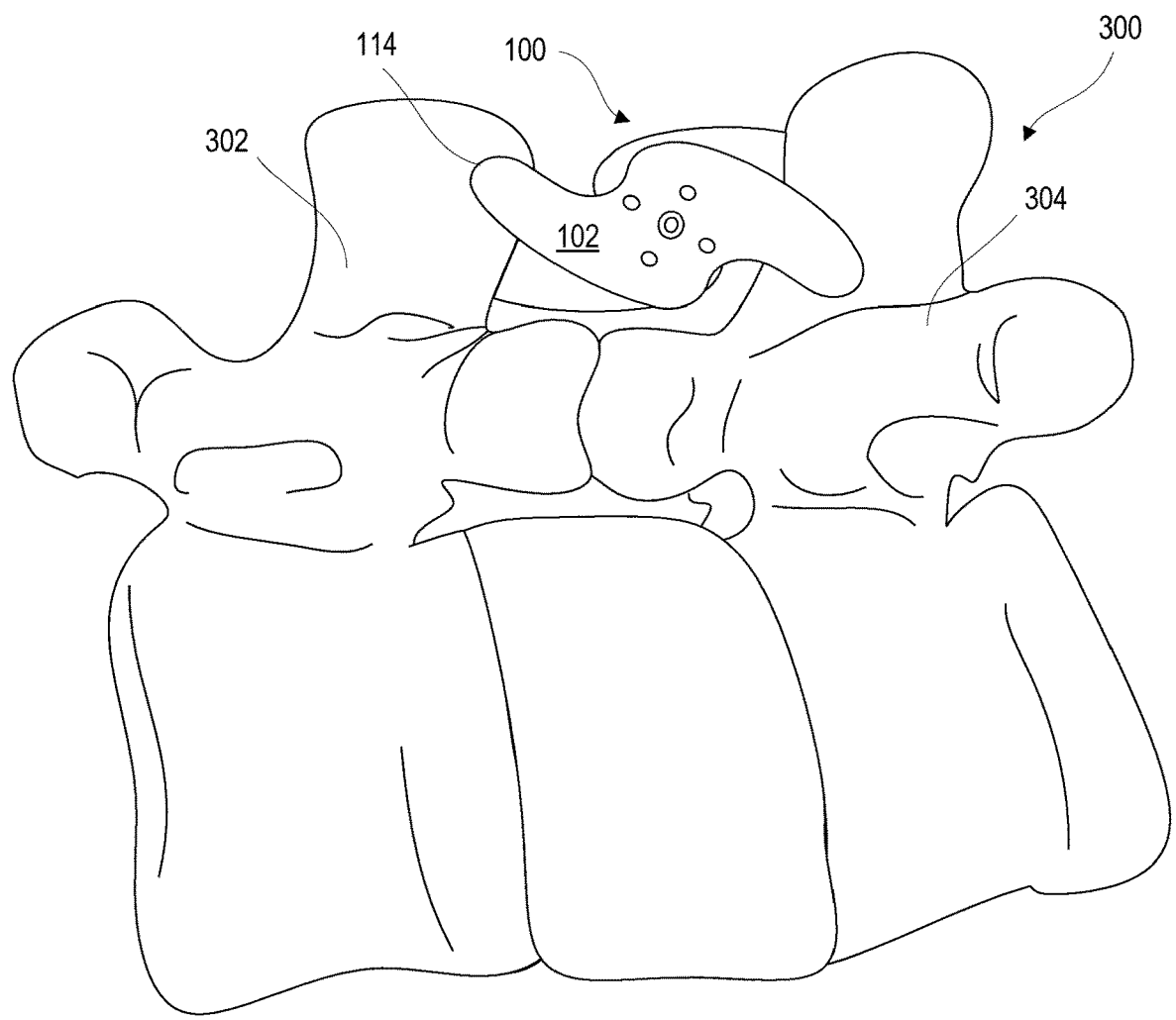
FIG. 11 shows the device of FIGS. 1-4 secured with and fusing adjacent vertebrae, according to an embodiment.
Figure 12:
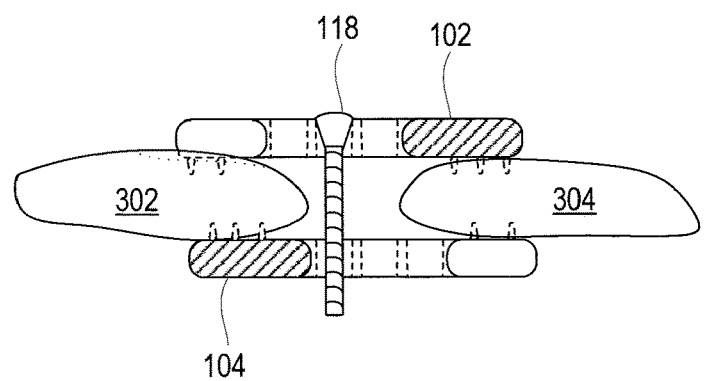
FIG. 12 is a cross-sectional top view showing the device of FIGS. 1-4 secured with and fusing adjacent vertebrae, according to an embodiment.

FIGS. 11 and 12 schematically illustrate device 100 mounted to fuse adjacent vertebrae 302, 304 of a spinal column 300, shown in part. As shown, plates 102, 104 may be rotated with respect to one another and still joined by a surgeon via bolt 118 through selected holes 106. Although not shown here, plates 102 and 104 may also be horizontally or vertically offset from one another. Adjustable bolt angles (described above) additionally allow for securing device 100 with plates 102 and 104 to be tilted in and out of plane with respect to one another, thus providing a wide range of plate positions. In practice, a surgeon may slide, rotate and tilt one or both of plates 102 and 104 along the spinous process(es), in order to find a "best fit" with the existing bone topography. Device 100 may therefore reduce or eliminate the shaving that is necessary to align prior art fixation devices with vertebral bone, thus preserving strength of the spinous processes and reducing complications associated with bone shaving, as well as reducing overall surgical time and complexity.

Figure 21:
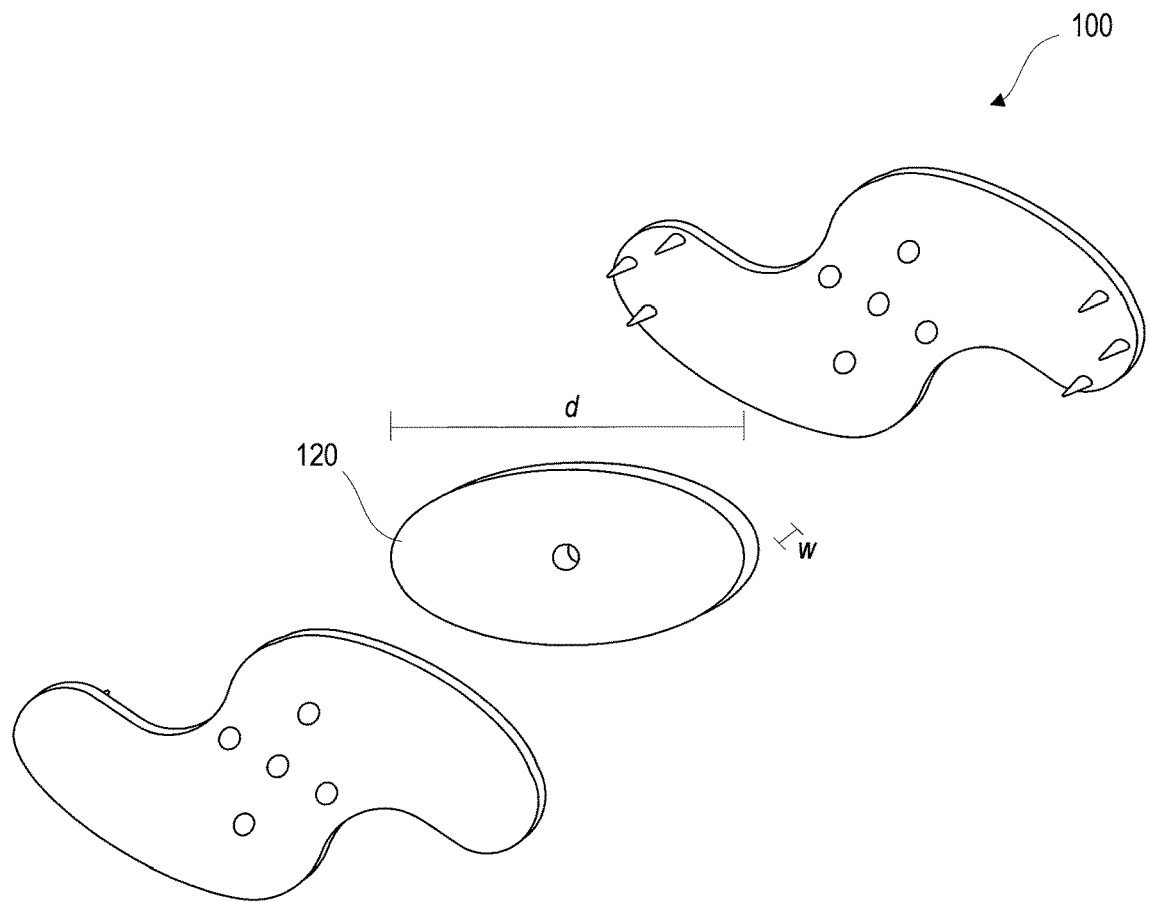
FIG. 21 is a perspective view showing the device of FIGS. 1-4 with an interspinous spacer, according to an embodiment.
Figure 22:
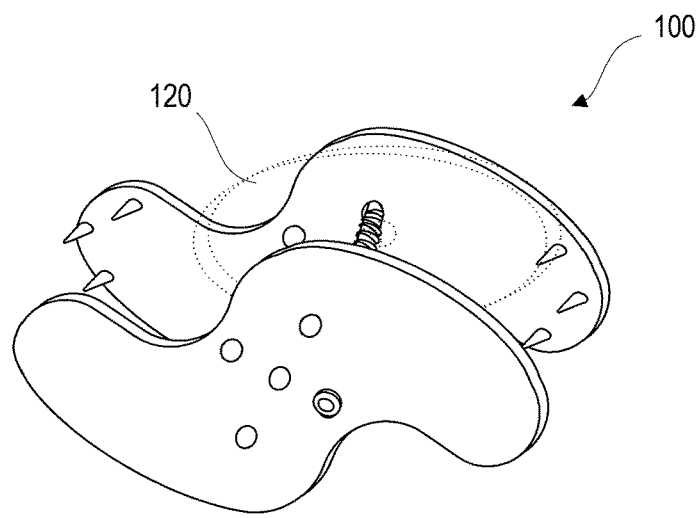
FIG. 22 shows the device and spacer of FIG. 21 joined with a bolt, according to an embodiment.

Optionally, where a surgeon wishes to distract adjacent spinal processes, bolt 118 additionally secures a spacer between plates 102 and 204. FIGS. 21 and 22 show one exemplary spacer 120, which may be made from PEEK plastic or other suitable, biocompatible material. Width of spacer 120 is selected to securely fit a desired space between plates 102 and 104. Diameter d of spacer 120 is selected according to the interspinous space between adjacent spinous processes. Spacer 120 width for example ranges from 4 to 10 mm, and diameter d may be between about 6 mm and 14 mm, depending upon the interspinous space and any additional decompression/distraction desired. It will be appreciated that although shown as an oval, spacer 120 may take a rounded or other geometric shape. Furthermore, although not shown here, spacer 120 may include surface features along its width (such as receiving channels) for fitting with spinous processes.

FIGS. 14-18 are similar to FIGS. 1-4 and 11, showing a device 400 that shares features of device 100, but has plates 402 and 404 with a squared-off shape compared to plates 102 and 104. Like numbers represent similar elements in FIGS. 14-18 and corresponding FIGS. 1-4 and 11. It will be appreciated that although not shown, a spacer such as spacer 120 may also be used with device 400.

Figure 19:
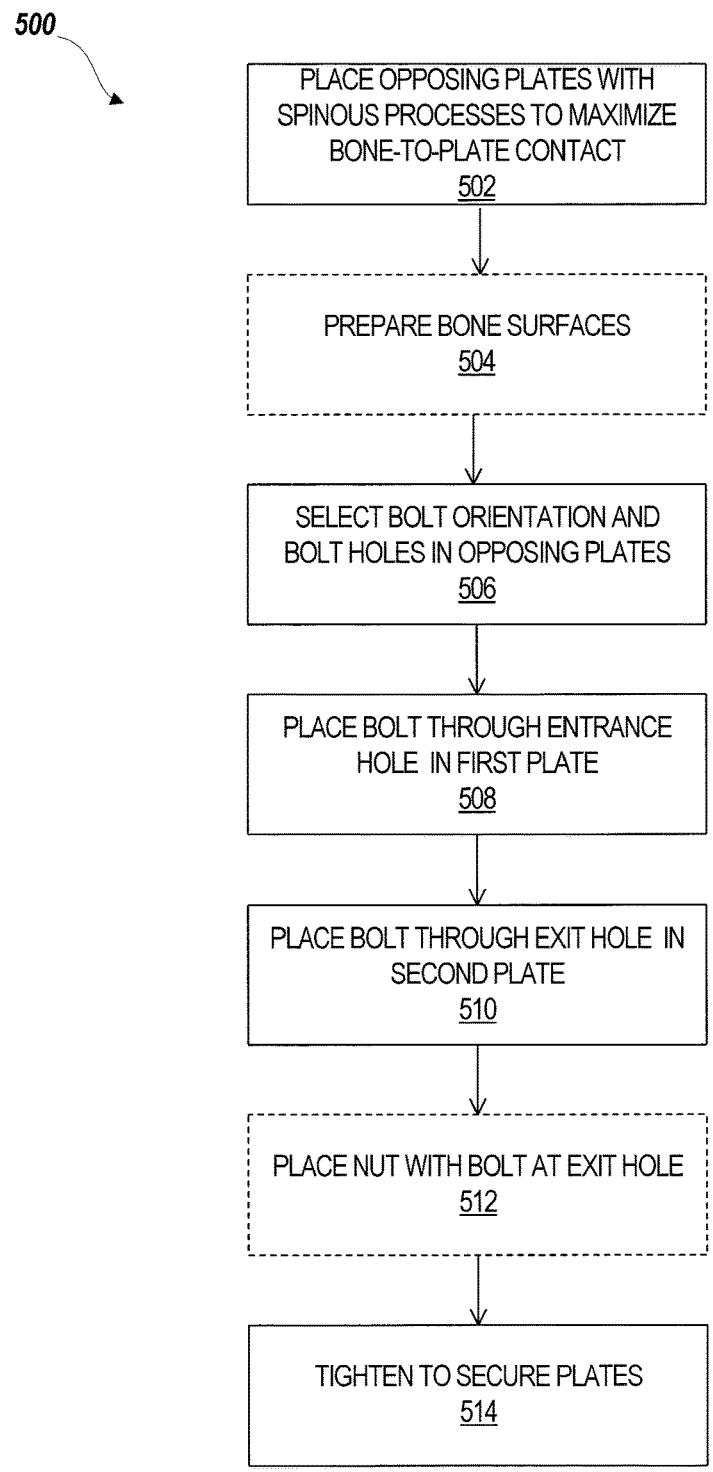
FIG. 19 depicts a method of vertebral fixation, according to an embodiment.

FIG. 19 illustrates a method 500 of spinal fixation. In step 502, opposing plates of a spinal fixation device are placed with spinous processes of adjacent vertebrae so as to maximize bone-to-plate contact. In one example of step 502, plates 102 and 104 of device 100 (or plates 402 and 404 of device 400) are rotated, tilted, moved laterally or moved horizontally with respect to the vertebral column to achieve a best fit with opposite sides of adjacent spinous processes. Receiving surfaces of the spinous processes are prepared, in optional step 504. In one example, one side of the spinous process of vertebra 302 (FIG. 11) is cleaned or otherwise prepared, but not shaved, where plate 102 may be tilted or rotated such that arm 114 lies substantially flush with existing bone. Likewise, where plate 102/104 may be manipulated to fit existing boney surfaces, shaving may be reduced or eliminated.

In step 506, a surgeon selects bolt orientation and entrance and exit bolt holes of plates 102, 104, in order to secure device 100 at the chosen orientation. The bolt is placed through the entrance hole in a first plate, and advanced between the plates and through the exit hole in the second plate, in steps 508 and 510. In one example, bolt 118 may be placed through hole 106C of plate 102 and through hole 106B of plate 104 (see FIG. 8). A nut may be used to secure the bolt in place, in step 512. The bolt is tightened to secure plates of the spinal fixation device in the desired orientation, in step 514 (for example, pressing prongs 512 into the bone).

Figure 20:
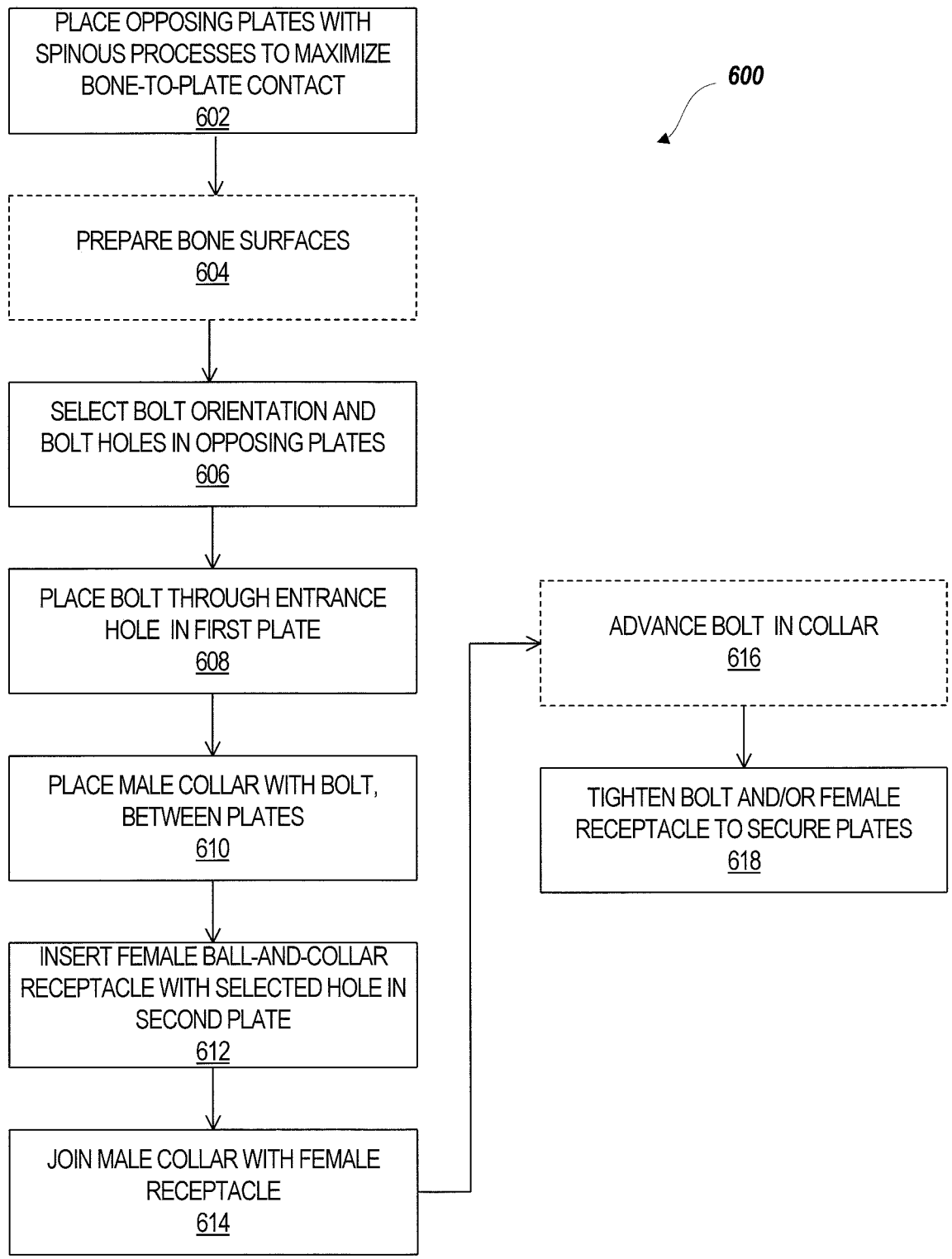
FIG. 20 depicts another method of vertebral fixation, according to an embodiment.

FIG. 20 illustrates a method 600 of spinal fixation utilizing a male and female connection system, such as system 200. Opposing plates are placed with spinous processes of adjacent vertebrae, in step 602, so as to maximize bone-to-plate contact. Bone surfaces are prepared as necessary in step 604, for example as described with respect to method 500, above. Bolt orientation and entrance and exit holes are selected in step 606, and the bolt is advanced through the entrance hole of one plate in step 608. A male collar of the male and female connection system is placed with the bolt, between the device plates, in step 610. For example, collar 204 is threaded at least partially onto bolt 118, between plates 102 and 104. A female ball-and-collar receptacle is inserted into the exit hole, in step 612. For example, receptacle 202 is inserted into a selected hole 106 from an outer side of plate 104. The male collar and female receptacle are joined together, in step 614. In one example, receptacle 202 is held in place via a hex key or other tool while collar 104 is rotated to join exterior threads of collar 104 with interior threads of receptacle 202. Screw 118 may be further tightened to advance the screw within the collar, in step 616. In step 618, the spinal fixation device is secured in its desired position by further tightening the bolt and/or female receptacle.

Figure 23:
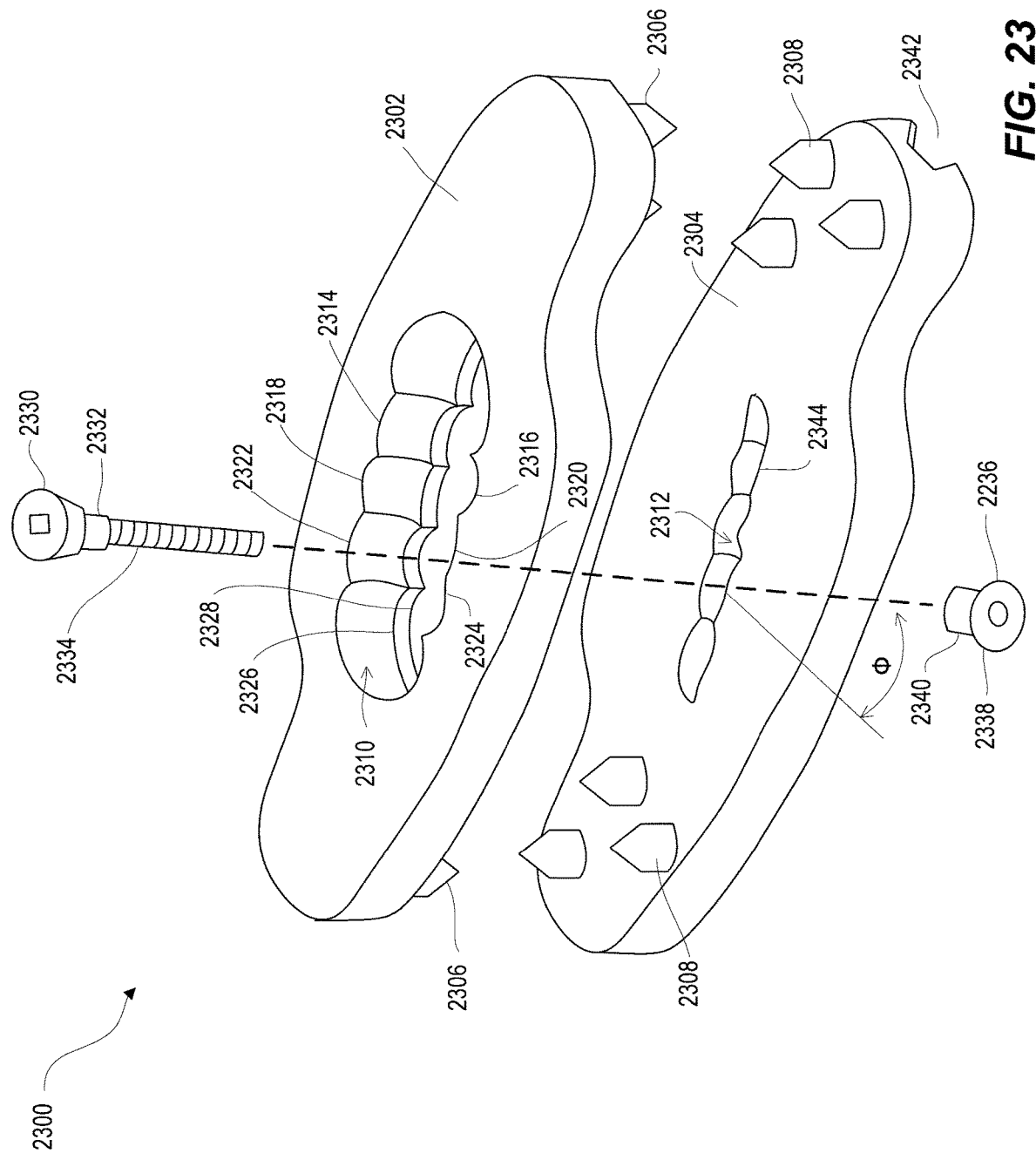
FIG. 23 is an assembly view that shows an alternative embodiment of a spinal fixation device.

FIG. 23 is an assembly view that shows an alternative embodiment of a spinal fixation device 2300. Plates 2302, 2304 have a generally S-shaped structure for stacking of plates as described above, together with pins 2306, 2308 for stabilizing plate to bone contact. Plate 2302 defines a central opening 2310 with opening 2312 in plate 2304 being a minor image of opening 2310. Opening 2310 has a plurality of opposed radiused knurls 2314-2316, 2318-2320, 2322-2324. These knurls taper centrally to narrow towards ridge 2326 which, in turn, narrows at an even sharper taper towards edge 2328. These structures in opening 2310 complement a tapered head 2330 and collar 2332 of bolt 2334. Nut 2336 has the same type of tapered head 2338 and collar 2340, where the nut 2336 may be slidingly engaged for retention in a tapered channel 2342 along a bottom surface of plate 2304. Tolerances between the bolt head 2330 and opening 2310, as well as tolerances between nut 2336 and opening 2312, permit the bolt 2334 and nut 2336 to joint plates 2302, 2304 at any angle Φ. By way of example, the nature of jointing may be angled such that head 2330 resides in knurl 2322 and nut 2336 resides in knurl 2344.

Figure 24:
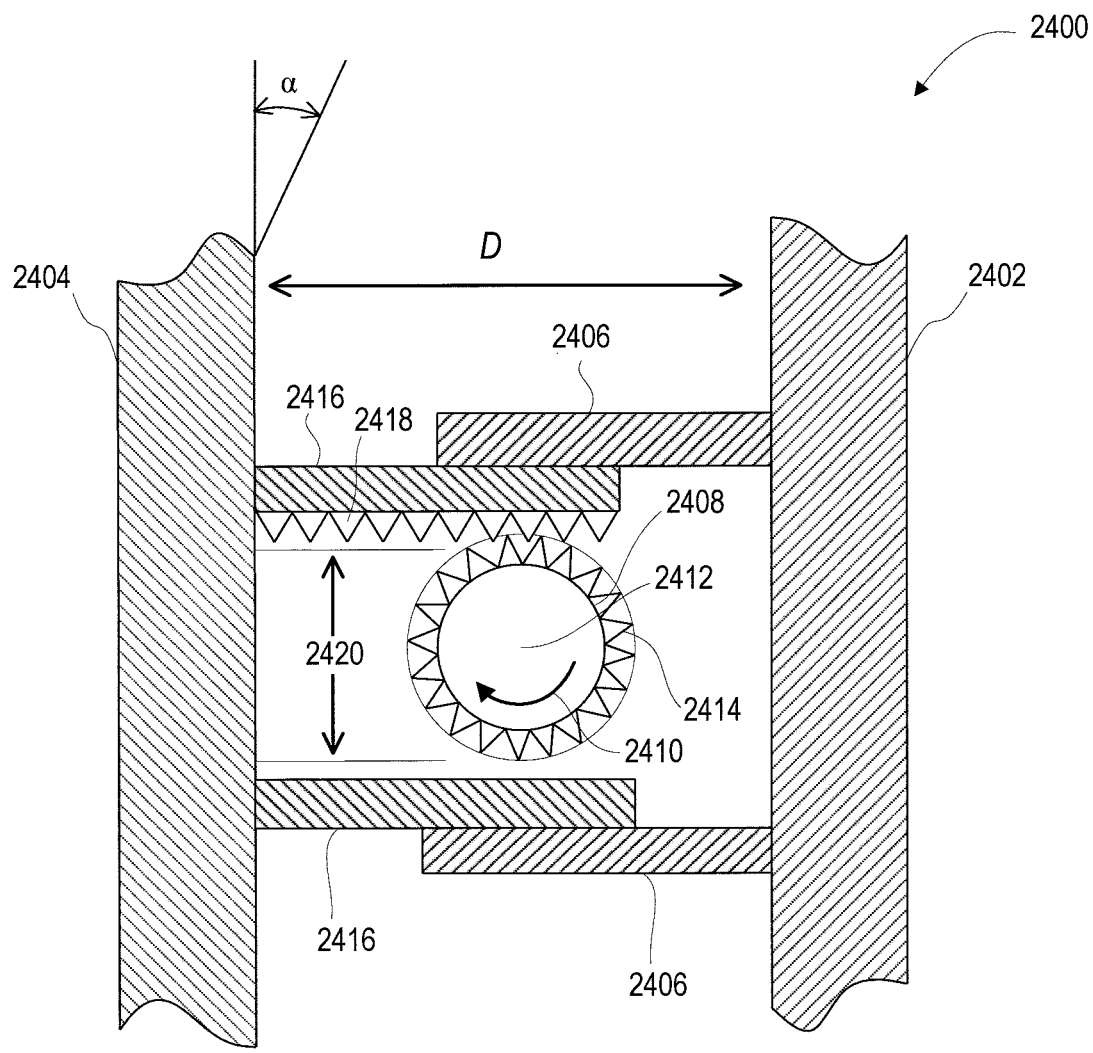
FIG. 24 is a midsectional view that shows an alternative clamping structure for use in a spinal fixation device.

FIG. 24 is a midsectional view that shows an alternate clamping mechanism 2400 that may be used to install plates 2402, 2404 on spinous process (not shown). Plate 2402 is integrally formed with a central tubular wall 2406. The wall 2406 carries a pinion gear assembly 2408 that may be turned on arc 2410 by engagement between a key (not shown) and a keyhole 2412. A ratchet-stop 2414 selectively retains gear assembly 2408 at a position of rotation on arc 2410. Plate 2404 is integrally formed with tubular wall 2416, which is telescopically received within tubular wall 2406. The wall 2416 carries a rack gear 2418 that engages the pinion gear assembly 2408 such that clockwise rotation of the pinion gear assembly 2408 on arc 2410 moves plates 2402, 2404 together, reducing distance D. Wall 2416 is provided with a slot for accommodating the pinion gear assembly 2408. As FIG. 24 is a midsectional view, the slot is not visible; however, exemplary position of the slot along a floor of tubular wall 2416 is indicated by a space 2420. It will be appreciated that the slot may be positioned within wall 2416 at a location other than space 2420. An opposing slot (not shown) in wall 2416 provides access to the keyhole 2412. Tolerances between the walls 2406, 2416 may permit the joining of plates 2402, 2404 in a relationship that is not necessary in parallel where, for example, plate 2404 may be tilted and an angle α relative to plate 2402.

While the present invention has been described above, it should be clear that many changes and modifications may be made to the process and product without departing from the spirit and scope of this invention.

What is claimed is:

1. A spinal fixation device comprising:
   a first plate with a substantially s-shape having an outer surface and a bone contact surface and a plurality of first plate apertures therethrough,
   a second plate with a shape substantially identical to the first plate having an outer surface and a bone contact surface and a plurality of second plate apertures therethrough such that each one of the plurality of first plate apertures has an aligned in a medial lateral direction and analogous one aperture of the plurality of second plate apertures when the first plate and second plate are aligned as mirror images; and
   a bolt extending in the medial-lateral direction from the bone contact surface of the first plate to the bone contact surface of the second plate for joining the first and second plates at a desired orientation through a selected aperture of the plurality of apertures, wherein in each of the plurality of first apertures and each of the plurality of second apertures are configured to receive the bolt, and wherein the bolt is configured to join the first and second plates through the selected apertures wherein the selected apertures are selected from the group of apertures consisting of: aligned and analogous apertures and non-aligned and non-analogous apertures;
   the bolt including a head with a rounded or beveled base for facilitating fixation of the plates with a spinous processes while the plates are tilted or rotated with respect to one another and the spinal column.

2. The device of claim 1, the plurality of apertures comprising beveled apertures.

3. The device of claim 1, the plates comprising titanium.

4. The device of claim 1, the plates comprising a biocompatible material having sufficient strength to fuse adjacent vertebrae of the spinal column.

5. The device of claim 1, the bone contact surfaces of each plate comprising one or more prongs for penetrating bone of the spinous process, to enhance fixation of the plates with the spinous process.

6. The device of claim 1, the rounded or beveled base of the bolt allowing variation in angles between the plates, when the plates are joined.

7. The device of claim 1, further comprising a nut for joining with a free end of the bolt to secure the plates about the spinous process.

8. The device of claim 1, the head of the bolt comprising an aperture or other surface feature for accepting a tool for tightening the bolt with the plates and an end nut.

9. The device of claim 1, the plates configured to secure a spacer therebetween.

10. A spinal fixation device comprising:
    a first s-shaped plate,
    a second s-shaped plate, wherein the first s-shaped plate and the second s-shaped plate form a pair of substantially identical s-shaped plates,
    each of the first s-shaped plate and the second s-shaped plate having a plurality of apertures therethrough, wherein each of the plurality of apertures on the first plate has at least one analogous aperture on the second plate and at least one non-analogous aperture on the second plate; and
    a single bolt extending in a medial/lateral direction for joining the plates at a desired orientation, and wherein each of the plurality of apertures in the first s-shaped plate and each of the plurality of apertures in the second s-shaped plate are configured to receive the single bolt, and wherein the single bolt is operatively sized to join the first plate via any one of the plurality of apertures on the first s-shaped plate and an aperture of the plurality of apertures on the second s-shaped plate selected from the group of apertures consisting of: the at least one analogous aperture and the at least one non-analogous aperture;
    the single bolt including a head with a rounded or beveled base for facilitating fixation of the plates with spinous processes while the plates are tilted or rotated with respect to one another and the spinal column.

11. The device of claim 10, the plurality of apertures through each plate tapering from an outer surface to a bone contact surface.

12. The device of claim 11, further comprising a tapered nut for securing with an end of the bolt, to secure the plates together about a spinous process.

13. The device of claim 12, the bolt head, nut and plurality of apertures configured with tolerances therebetween that permit joining of the plates, bolt and nut at a variety of angles.

* * * * *